United States Patent
Tavakoli et al.

(10) Patent No.: US 9,629,615 B1
(45) Date of Patent: Apr. 25, 2017

(54) COMBINED B-MODE / TISSUE DOPPLER APPROACH FOR IMPROVED CARDIAC MOTION ESTIMATION IN ECHOCARDIOGRAPHIC IMAGES

(71) Applicant: University of Louisville Research Foundation, INc., Louisville, KY (US)

(72) Inventors: Vahid Tavakoli, Louisville, KY (US); Amir A. Amini, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 56 days.

(21) Appl. No.: 14/480,313

(22) Filed: Sep. 8, 2014

Related U.S. Application Data

(60) Provisional application No. 61/874,454, filed on Sep. 6, 2013.

(51) Int. Cl.
*A61B 8/00* (2006.01)
*A61B 8/08* (2006.01)
*G06T 7/00* (2006.01)

(52) U.S. Cl.
CPC .......... *A61B 8/5223* (2013.01); *A61B 8/0883* (2013.01); *A61B 8/463* (2013.01); *A61B 8/488* (2013.01); *G06T 7/0012* (2013.01)

(58) Field of Classification Search
CPC ..... A61B 8/5223; A61B 8/0883; A61B 8/463; A61B 8/488; G06T 7/0012
See application file for complete search history.

(56) References Cited

PUBLICATIONS

Dalen et al. "Segmental and global longitudinal strain and strain rate based on echocardiography of 1266 healthy individuals: the HUNT study in Norway". European Journal of Echocardiography (2010) 11, 176-183.*
Fred, D., et al., Essentials of nuclear medicine imaging, Fifth edition, W.B. Saunders, Philadelphia, 2005, 131-192.
Webb, A. Introduction to Biomedical Imaging, John Wiley and Sons Inc., Hoboken, NJ, 2003.
ASE Guidelines and Standards—Journal of the American Society of Echocardiography, vol. 28, No. 1, pp. 11-39.

(Continued)

*Primary Examiner* — Michael Rozanski
(74) *Attorney, Agent, or Firm* — Stites & Harbison, PLLC; Jeffrey A. Haeberlin; Terry L. Wright

(57) ABSTRACT

A method for cardiac motion estimation includes: receiving a set of echocardiographic images of a heart, the echocardiographic images including B-mode ultrasonic images and Tissue Doppler Imaging (TDI) images; and calculating, by the image processing machine, a motion field representing the motion of the heart using the B-mode ultrasonic images and applying a velocity constraint from the TDI images. A system for cardiac motion estimation, includes: an imaging device configured to acquire a set of echocardiographic images of a heart, the echocardiographic images including B-mode ultrasonic images and TDI images; a data storage device in communication with the imaging device and configured to store the set of echocardiographic images; an image processing machine in communication with the data storage device and configured to calculate a motion field representing the motion of the heart using the B-mode ultrasonic images and applying a velocity constraint from the TDI images.

13 Claims, 16 Drawing Sheets

(56) References Cited

PUBLICATIONS

Suhling, M., Arigovindan, A., et al.: Myocardial motion analysis from B-mode echocardiograms. IEEE Transaction on Image Processing, vol. 14, No. 2, pp. 525-553 (2005).
Yu, W., Yan, P., Sinusas, A. J., Thiele, K., Duncan, J. S.: Towards point-wise motion tracking in achocardiographic image sequences—Comparing the reliability of different features for speckle tracking. Medical Image Analysis, vol. 10, No. 4, pp. 495-508 (2006).
Paragios, N.: A level set approach for shape-driven segmentation and tracking of the left ventricle. Medical Imaging, IEEE Transactions on, vol. 22, No. 6, pp. 773-776, Jun. 2003.
Hayat, D., Kloeckner, M., Nahum, J., Ecochard-Dugelay, E., Dubois-Rande, J.L., Jean-Francois, D. et al., Comparison of real-time three-dimensional speckle tracking to magnetic resonance imaging in patients with coronary heart disease, Am J Cardiol, 109 (2012), pp. 180-186.
Elen, A., Choi, H.F., Loeckx, D., Gao, H., Claus, P., Suetens, P., Maes, F., D'Hooge, J. Three-Dimensional cardiac strain estimation using spatio-temporal elastic registration of ultrasound images: A feasibility study. IEEE Transaction Medical Imaging, 27(11) (2008) 1580-1591.
Esther Leung, K.Y., Danilouchkine, M.G., Van Stralen, M., De Jong, N., Van Der Steen, A.F.W., Bosch, J. G. Probabilistic framework for tracking in artifact-prone 3D echocardiograms, Medical Image Analysis, 14 (6) (2010) 750-758.
Myronenko, A., Song, X. Point Set Registration: Coherent Point Drift, IEEE Transaction on Pattern Analysis and Machine Intelligence, 32 (12) (2010) 2262-2275.
Duchateau, N., De Craene, M., Piella, G., Silva, E., Doltra, A., Sitges, M., Bijnens, B.H., Frangi, A. F. A spatiotemporal statistical atlas of motion for the quantification of abnormal myocardial tissue velocities, Medical Image Analysis, 15(3) (2011) 316-328.
Bachner-Hinenzon, N., Ertracht, O., Lysiansky, M., Binah, O., Adam, D. Layer-specific assessment of left ventricular function by utilizing wavelet de-noising: a validation study, Medical and Biological Engineering and Computing,49(1) (2011) 3-13.
Dydenko, I., Jamal, F., Bernard, O., D'Hooge, J., Magnin, I.E., Friboulet, D. A level set framework with a shape and motion prior for segmentation and region tracking in echocardiography, Medical Image Analysis, 10(2) (2006) 162-177.
Yan, P., Sinusas, A., Duncan, J.S. Boundary element method-based regularization for recovering of LV deformation, Medical Image Analysis11 (6) (2007) 540-554.
De Craene, M., Piella, G., Camara, O., Duchateau, N., Silva, E., Doltra, A., D'Hooge, J., Brugada, J., Sitges, M., Frangi, A. Temporal diffeomorphic free form deformation application to motion and strain estimation from 3D echocardiography, Medical Image Analysis, 16(2) (2012) 427-450.
Ashraf, M., Myronenko, A., Nguyen, T., Inage, A., Smith, W., Lowe, R.I., et al., Defining left ventricular apex-to-base twist mechanics computed from high-resolution 3D echocardiography: validation against sonomicrometry, JACC Cardiovasc Imaging, 3 (2010), pp. 227-234.
Papademetris, X., Sinusas, A.J., Dione, P., Constable, R. T., Duncan, J. S. Estimation of 3-D left ventricular deformation from medical images using biomechnical models, IEEE Transaction on Medical Imaging, 21(7) (2002) 786-800.
Tavakoli,V., et al., A Two-Chamber Multi-modal (MR/Ultrasound) Cardiac Phantom for Normal and Pathologic Hearts, International Society of Magnetic Resonance in Medicine (ISMRM), 2012.
Kleijn, S.A., Brouwer, W.P., Aly, M.F., Russel, I.K., De Roest, G.J., Beek, A.M., et al., Comparison between three-dimensional speckle-tracking echocardiography and cardiac magnetic resonance imaging for quantification of left ventricular volumes and function, Eur Heart J Cardiovasc Imaging, 13 (2012), pp. 834-839.
Garcia, D., Del Álamo, J.C., Tanné, D., et al: Two-Dimensional Intraventricular Flow Mapping by Digital Processing Conventional Color-Doppler Echocardiography Images. Medical Imaging, IEEE Transactions on, vol. 29, No. 10, pp. 1701-1713 (2010).
Dalen, H., Thorstensen, A., Aase, SA., Ingul, C.B., et al. : Segmental and global longitudinal strain and strain rate based on echocardiography of 1266 individuals: the HUNT study in Norway. Eur J Echocardiogr. vol. 11, No. 2, pp. 76-83 (2010).
Amundsen , B.H., Crosby, J., Steen, P.A., Torp, H., Slordahl, S.A., Stoylen, A. : Regional myocardial long-axis strain and strain rate measured by different tissue Doppler and speckle tracking echocardiography methods: a comparison with tagged magnetic resonance imaging. Eur J Echocardiogr, vol. 10, pp. 229-237 (2009).
Tavakoli, V., Kemp, J., Dawn, B., Stoddard, M., Amini, A. Comparison of myocardial motion estimation methods based on simulated echocardiographic B-mode and RF data. SPIE Medical Imaging, 76260N, 2010.
Gao, H., Choi, H.F., Claus, P., Boonen, S., et al.: A fast convolution-based methodology to simulate 2-D/3-D cardiac ultrasound images. IEEE Transactions on Ultrasonics, Ferroelectrics and Frequency Control, vol. 56, No. 2, pp. 404-409, Feb. 2009.
Arts, T., Hunter, W.C., Douglas, A., Muijtjens, A.M.M., Reneman R.S. Description of the Deformation of the Left Ventricle by a Kinematic Model. J. Biomechanics, vol. 25, No. 10, pp. 1119-1127 (1992).
Tustison, N.J.. Roman, V.G.D., Amini, A.A. Myocardial kinematics from tagged MRI based on a 4-D B-s;line Model, IEEE Transaction on Biomedical Engineering, 50 (8) (2003) 1038-1040.
Jensen, J.A., Svendsen, N. B. Calculation of pressure fields from arbitrarily shaped, apodized, and excited ultrasound transducers, IEEE Trans. Ultrason., Ferroelec., Freq. Contr., 39, pp. 262-267, 1992.
Tavakoli, V.; Negahdar, M.J.; Kendrick, M.; Alshaher, M.; Stoddard, M.; Amini, A.A.; , "A biventricular multimodal (MRI/ultrasound) cardiac phantom," Engineering in Medicine and Biology Society (EMBC), 2012 Annual International Conference of the IEEE , vol., no., pp. 3187-3190, Aug. 28, 2012-Sep. 1, 2012.
Lesniak-Plewinska, B., Cygan, S., Kaluzynski, K., D'Hooge, J., Zmigrodzki, J., Kowali, E., Kordybac, M., Kowalski, M. A Dual-Chamber, Thick-Walled Cardiac Phantom for Use in Cardiac Motion and Deformation Imaging by Ultrasound. Ultrasound in Medicine & Biology, vol. 36, Issue 7, pp. 1145-1156, 2010.
Geman, S., McClure, D.E.: Statistical methods for tomographic image reconstruction. Bull. Int. Statist. Int., vol. 52, pp. 5-21 (1987).
Arts, T., Prinzen, F.W., Delhaas, T., Milles, J., Rossi, A., Clarysse, P. Mapping displacement and deformation of the heart with local sine wave modeling. IEEE Trans Med Imag May 2010;29(5):1114-23.
Cho, G-Y, Chan, J., Leano, R., Strudwick, M., Marwick, T.H. Comparison of Two-Dimensional Speckle and Tissue Velocity Based Strain and Validation With Harmonic Phase Magnetic Resonance Imaging. The American Journal of Cardiology, vol. 97, Issue 11, Jun. 1, 2006, pp. 1661-1666.
Liu, C. Beyond pixels: exploring new representations and applications for motion analysis. Doctoral Thesis, Appendix A. Massachusetts Institute of Technology, May 2009.
Horn, B.K.P., Schunck, B.G. Determining optical flow. Artificial Intelligence, vol. 17, pp. 185-203 (1981).
Abolhassani, M.D., Tavakoli, V. Optimized Thermal Change Monitoring in Renal Tissue during Revascularization Therapy. Journal of Ultrasound in Medicine, No. 28, Issue 11, pp. 1535-1547, 2009.
Jasaityte, R., Heyde, B., D'Hooge, J. Current State of Three-Dimensional Myocardial Strain Estimation Using Echocardiography. Journal of the American Society of Echocardiography: official publication of the American Society of Echocardiography, vol. 26, issue 1, pp. 15-28, 2013.
Tustison, N.J., Amini, A.A. Biventricular myocardial strains via nonrigid registration of anatomical NURBS models, IEEE Transaction on Medical Imaging, 25(1) (2006) 94-112.
Dalen, H., Thorstensen, A., Romundstad, P., Aase, S., et al. : Cardiovascular Risk Factors and Systolic and Diastolic Cardiac Function: A Tissue Doppler and Speckle Tracking

(56) References Cited

OTHER PUBLICATIONS

Echocardiographic Study. J Am. Soc. Echocardiogr. vol. 24, No. 3, pp. 322-332e.6 (Mar. 2011).

* cited by examiner

FIG. 23    FIG. 24
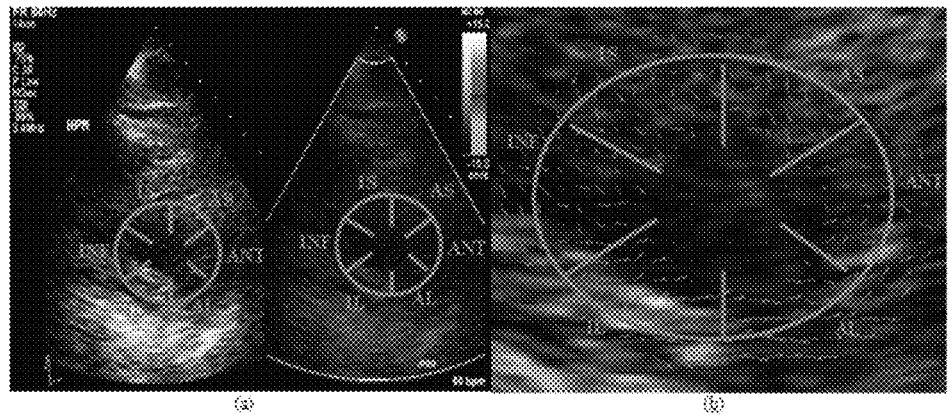
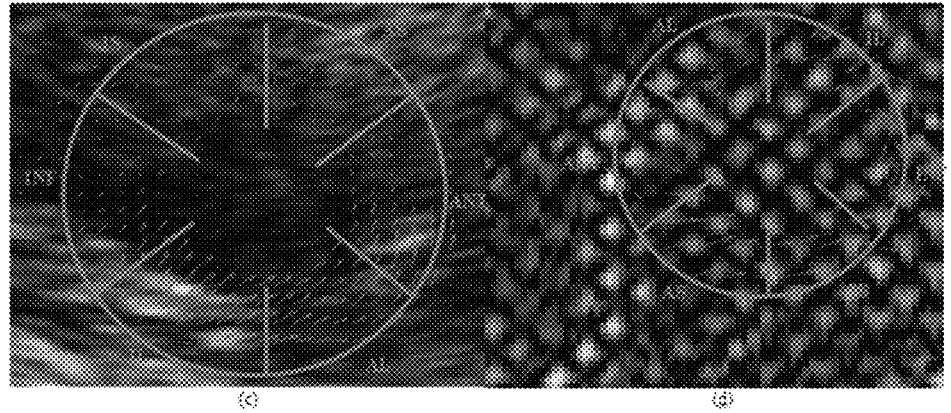
FIG. 25    FIG. 26

COMBINED B-MODE / TISSUE DOPPLER APPROACH FOR IMPROVED CARDIAC MOTION ESTIMATION IN ECHOCARDIOGRAPHIC IMAGES

RELATED APPLICATIONS

This application claims priority to U.S. Provisional Patent Application No. 61/874,454, filed Sep. 6, 2013, the entire disclosure of which is incorporated herein by reference.

STATEMENT REGARDING FEDERALLY SPONSORED RESEARCH OR DEVELOPMENT

Not applicable.

TECHNICAL FIELD

The presently-disclosed subject matter relates to cardiac motion estimation in echocardiographic images and to a combined B-Mode/Tissue Doppler approach for improved cardiac motion estimation in such images.

BACKGROUND

Cardiovascular Disease (CVD) is the leading cause of death in the modern world. The mortality rate associated with CVD was estimated to be 17 million in 2005 and continues to be ranked as the top killer worldwide. CVD is the result of under-supply of the cardiac tissue and can lead to malfunction of the involved myocardial territories and manifest as hypokinesia or akinesia. Several imaging methods such as X-ray CT, MRI, and Ultrasound have been used for visualization of the heart function. MRI and X-ray CT provide excellent spatial resolution but the cost and lack of wide-spread availability cause challenges in the clinical settings. Echocardiography is a popular technique for cardiac imaging due to its availability, ease of use, and low cost. Echocardiography shows the motion and anatomy of the heart in real time, enabling physicians to detect different pathologies. However, analysis of motion of the myocardium in echocardiographic images is based on visual grading by an observer and suffers from inter and intra-observer variability.

BRIEF SUMMARY OF THE INVENTION

To overcome the inter- and intraobserver variability, computerized image analysis can help by quantitatively interpreting the data. To that end, cardiac image processing techniques, mainly categorized as segmentation and registration, can be used for assessing the regional function of the heart [1][2][3]. To perform such analysis, two independent techniques have been utilized; these are tissue Doppler imaging (TDI) and speckle tracking. TDI computes the tissue motion based on the Doppler phenomenon and is dependent on the angle of insonification. Speckle tracking, on the other hand, is an image processing method based on the analysis of the ultrasound B-mode or RF images. B-mode-based algorithms are robust to the variation of the ultrasound beam angle but rely entirely on the properties of echocardiographic images which may be noisy or suffer from artifacts. The physical principle underlying B-mode and TDI is to a large degree independent and, therefore, carries complementary information for myocardial motion estimation [4][5].

Many methods such as optical flow [6], feature tracking [7], level sets [8], block matching [9], and elastic registration [10] have been utilized for quantitative assessment of myocardial motion in B-mode images. Table 1 shows a description of some of the current methods used in motion estimation in echocardiographic images [6]-[21]. Suhling et al. [6] integrated rigid registration in an optical flow framework in order to detect myocardial motion from 2D echocardiographic images. B-spline moments invariants were applied to echo images to achieve invariance to the translation and rotation. The motion estimation algorithm was then applied to the B-spline moments of the image instead of the image intensity in a coarse to fine strategy and was validated using open chested dogs after ligation of a coronary artery. Additional validations were performed on simulation and phantom images. Ellen et al. [10] used elastic registration on 3D B-mode echocardiography images to extract myocardial motion and strain values. The method was validated using simulated and real ultrasound images. Esther-Leung et al. [11] proposed two different methods (1. model-driven, 2. edge-driven) for tracking the left-ventricular wall in echocardiographic images. Their approach was motivated by the fact that in echocardiography images, visibility of the myocardium depends on the imaging view; so the myocardium may be, partly, invisible to the beam. Their technique relied on a local data-driven tracker using optical flow applied to the visible parts of the myocardium and a global statistical model applied to the invisible parts. It was concluded that the shape model could render good results for both the visible and the invisible tissues in ultrasound images. Myronenco et al. [12] proposed the so-called Coherent Point Drift (CPD) technique for myocardial motion estimation, constraining the motion of the point set in the temporal direction for both rigid and nonrigid point set registration. A set of point distribution was computed based on endocardium and epicardium locations. The point set was modeled with a Gaussian mixture model (GMM). The GMM centroids were updated coherently in a global pattern using maximum likelihood to preserve the topological structure of the point sets. A motion coherence constraint was added based on regularization of the displacement fields. The purpose of regularization was to increase the motion smoothness.

TABLE 1

DESCRIPTION OF SOME OF THE CURRENT METHODS USED IN MOTION DETECTION IN ECHOCARDIOGRAPHY IMAGES

| Article | Output | Technique | Validation (# of subjects) |
|---|---|---|---|
| Suhling et al [6] | Motion | B-spline moments, Optical flow | 2D Dog (6), Simulated images, Phantom |
| Yu et al. [7] | Motion | Maximum Likelihood, Spline based control points | 2D Dog (4), Sonomicrometry |

TABLE 1-continued

DESCRIPTION OF SOME OF THE CURRENT METHODS USED IN MOTION DETECTION IN ECHOCARDIOGRAPHY IMAGES

| Article | Output | Technique | Validation (# of subjects) |
|---|---|---|---|
| Paragios [8] | Endocardium, Motion | Level set + learned shape-motion prior | 2D Human |
| Hayat et al [9] | Motion | Block Matching | 3D echo, MRI |
| Elen et al [10] | Motion | Elastic registration | 3D Human (Normal: 3, Patient: 1), Simulated images |
| Esther Leung et al. [11] | Motion | Optical flow and shape model | 3d ECHO |
| Myronenco et al. [12] | Motion | Motion coherence by temporal regularization | 3D Human, EB |
| Duchateau et al [13] | Motion | Diffeomorphic registration | 2D Human (Normal: 21, Patient: 14), |
| Bachner et al [14] | Motion | Fiber direction | 2D Human, Simulation, phantom |
| Dydenco et al [15] | Epicardium, Motion | Regional statistics curve evolution | 2D Human, TDI |
| Van et al [16] | Epicardium, Motion | Finite Element Model | 3D Human, Implanted marker |
| De Craene et al [17] | Epicardium | Diffeomorphic B-Spline Free Form Deformation | 3D Human (Normal:9, Patient:13) |
| Ashraf et al [18] | Motion | 3D Pig | Sonomicrometry |
| Papademetris [19, 20] | Motion | Finite Element Model | 3D Echo |
| Kleijn et al. [21] | Motion | Block Matching | 3D echo |

Most of the motion estimation techniques developed thus far, are either based on TDI or B-mode. Recently, Garcia et al. [22] considered the combination of cardiac B-mode images and intra-cardiac blood flow data for computing the blood flow motion in the heart using continuity equation and mass conservation in polar coordinates. Their paper focused on the blood flow computation and did not consider the cardiac tissue displacements. Dalen et al. [23] and Amundsen et al. [24] previously combined TDI with speckle tracking by integrating TDI in the beam direction and speckle tracking in the direction lateral to the beam. However, this method discarded the speckle tracking data in the beam direction. The authors reported that they were unable to improve the motion estimation performance compared to speckle tracking techniques. Herein, the inventors describe integration of tissue Doppler and speckle tracking within a novel optical flow framework, called TDIOF (Tissue Doppler Optical Flow). Experimental results indicate that TDIOF outperforms both TDI and speckle tracking approaches.

According to one aspect of the invention, a method for cardiac motion estimation includes: receiving, by an image processing machine, a set of echocardiographic images of a heart, the echocardiographic images including B-mode ultrasonic images and Tissue Doppler Imaging (TDI) images; and calculating, by the image processing machine, a motion field representing the motion of the heart using the B-mode ultrasonic images and applying a velocity constraint from the TDI images.

In one embodiment, calculating the motion field utilizes an optical flow energy function which combines: B-mode intensity constancy; motion smoothness; and Doppler/B-mode velocity similarity.

The B-mode intensity constancy may be formulated as:

$$E_{data}=|I(p+w+dw)-I(p)|^2$$

where:
p=(x, y, t) and the flow field is w(p)=(u(p),v(p),1) where u and v are the motion vectors and x, y, and t are the spatial and temporal dimensions;

I(p) is the pixel intensity at location p and I(p+w) is the pixel intensity from a subsequent image at location p+w, assuming that the pixel intensity is the same along the motion vector; which is linearized using Taylor series expansion as:

$$I_t(p+w+dw)-I(p)=I_t(p)+I_x(p)du(p)+I_y(p)dv(p)$$

with $$I_x(p) = \frac{\partial I(p+w)}{\partial x}$$
$$I_y(p) = \frac{\partial I(p+w)}{\partial y}$$

$$I_t(p)=I(p+w)-I(p)$$

Motion smoothness may be formulated as:

$$E_s=|\nabla(u+du)|^2+|\nabla(v+dv)|^2$$

with $$|\nabla(u+du)|^2 = \left(\frac{\partial(u+du)}{\partial x}\right)^2 + \left(\frac{\partial(u+du)}{\partial y}\right)^2.$$

Doppler/B-mode velocity similarity may be formulated as:

$$E_{tdi}=(\vec{v}^T\vec{v}_t-w_{tdi})^2=(u_tu+v_tv-w_{tdi})^2$$

where:
$\vec{v}=(u, v)$ is the B-mode velocity;
$\vec{v}_t=(u_t, v_t)$ is the transducer orientation; and
$w_{tdi}$ is the TDI velocity.

The energy function to be minimized is then:

$$E(u, v) = E_{data} + \alpha E_s + \beta \psi(E_{tdi}) =$$

$$\int_\Omega (|I(P+w+dw) - I(p)|^2 + \alpha(|\nabla(u+du)|^2 + |\nabla(v+dv)|^2) +$$

$$\beta \cdot \psi((u_t(u+du) + v_t(v+dv) - w_{tdi})^2))$$

where:

α is the smoothness weight;

β is the TDI/velocity correspondence parameter; and

ψ(s) is a Geman-Mcclure penalizer to keep the range of $E_{tdi}$ between 0 and 1 where s is the input data, σ is the scaling parameter, and $$\psi(s) = \frac{s^2}{s^2 + \sigma^2}.$$

In one implementation, u, v, du, and dv are vectorized as U, V, dU, and dV, and the energy function is discretized. Then u, v, dU, and dV may be initialized as 0, with dU and dV iteratively updated using linear least squares. Additionally, calculating the motion field may be performed in a multiscale strategy, with a course scale used in an initial step and a fine scale is used in a subsequent step.

According to another aspect of the invention, a system for cardiac motion estimation, includes: an imaging device configured to acquire a set of echocardiographic images of a heart, the echocardiographic images including B-mode ultrasonic images and Tissue Doppler Imaging (TDI) images; a data storage device in communication with the imaging device and configured to store the set of echocardiographic images; an image processing machine in communication with the data storage device and configured to calculate a motion field representing the motion of the heart using the B-mode ultrasonic images and applying a velocity constraint from the TDI images.

In one implementation, the image processing machine calculates the motion field utilizing an optical flow energy function which combines: B-mode intensity constancy; motion smoothness; and Doppler/B-mode velocity similarity.

B-mode intensity constancy, motion smoothness, and Doppler/B-mode velocity similarity may be formulated as discussed above, and the energy function to be minimized may also be as discussed above.

In one implementation, u, v, du, and dv are vectorized as U, V, dU, and dV, and the energy function is discretized. Then u, v, dU, and dV may be initialized as 0, with dU and dV iteratively updated using linear least squares. Additionally, calculating the motion field may be performed in a multiscale strategy, with a course scale used in an initial step and a fine scale is used in a subsequent step.

According to another implementation, the system further includes an output device in communication with the image processing machine and configured to display the motion field representing the motion of the heart.

Further advantages of the presently-disclosed subject matter will become evident to those of ordinary skill in the art after a study of the description, Figures, and non-limiting Examples in this document.

BRIEF DESCRIPTION OF THE DRAWINGS

FIG. 23 is an image showing B-mode and TDI images in early systole at the high papillary muscle level of a subject.

FIG. 24 is an image showing the computed motion of the heart between two frames using the Horn-Schunck optical motion field.

FIG. 25 is an image showing the computed motion of the heart between two frames using the TDIOF motion field.

FIG. 26 is an image showing the tagged MRI motion field for the same approximate slice location in systole.

DETAIL DESCRIPTION OF EXEMPLARY EMBODIMENTS

Figure 1:
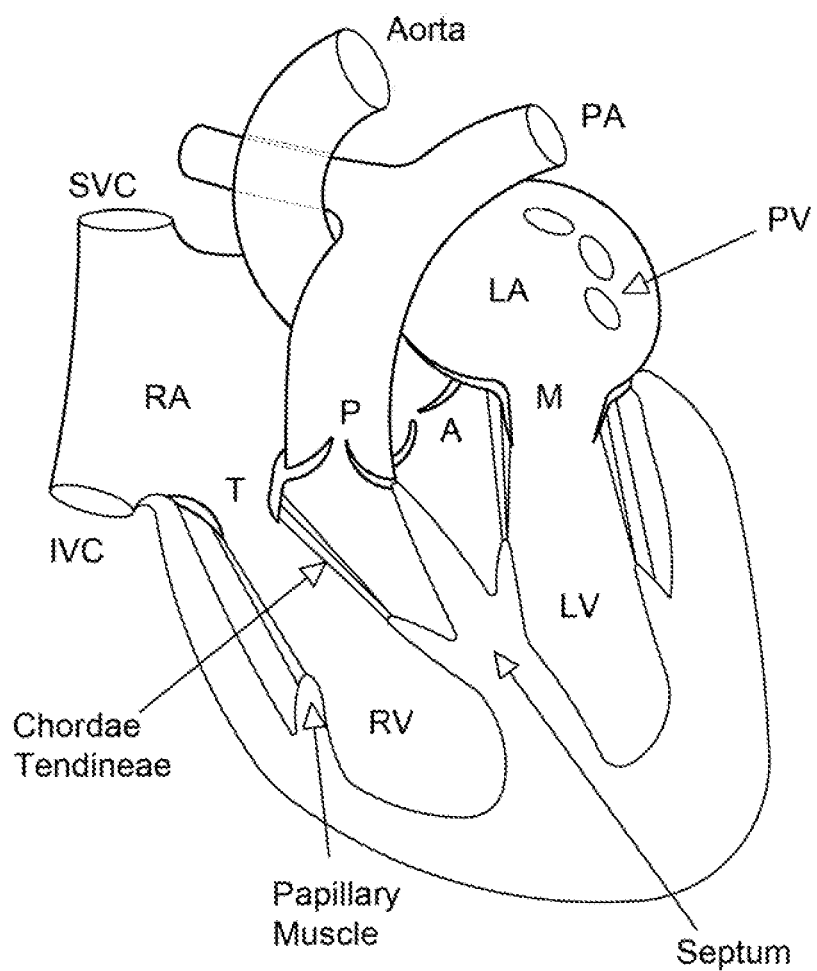
FIG. 1 is a schematic representation of a heart.

The details of one or more embodiments of the presently-disclosed subject matter are set forth in the attachments to this document. Modifications to embodiments described in these attachments, and other embodiments, will be evident to those of ordinary skill in the art after a study of the information provided in these attachments. The information provided in these attachments, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "image processing machine" is used herein to describe one or more microprocessors, microcontrollers, central processing units, Digital Signal Processors (DSPs), Field-Programmable Gate Arrays (FPGAs), Application-Specific Integrated Circuits (ASICs), or the like for executing instructions stored on a data storage device.

The term "data storage device" is understood to mean physical devices (computer readable media) used to store programs (sequences of instructions) or data (e.g. program state information) on a non-transient basis for use in a computer or other digital electronic device, including primary memory used for the information in physical systems which are fast (i.e. RAM), and secondary memory, which are physical devices for program and data storage which are slow to access but offer higher memory capacity. Traditional secondary memory includes tape, magnetic disks and optical discs (CD-ROM and DVD-ROM). The term "memory" is often (but not always) associated with addressable semiconductor memory, i.e. integrated circuits consisting of silicon-based transistors, used for example as primary memory but also other purposes in computers and other digital electronic devices. Semiconductor memory includes both volatile and non-volatile memory. Examples of non-volatile memory include flash memory (sometimes used as secondary, sometimes primary computer memory) and ROM/PROM/EPROM/EEPROM memory. Examples of volatile memory include dynamic RAM memory, DRAM, and static RAM memory, SRAM.

Optical flow is the pattern of apparent motion of objects, surfaces, and edges in a visual scene caused by the relative motion between an observer and the scene. Image registration, on the other hand, is a process of determining an optimal spatial mapping that matches images collected at different times or using different imaging modalities, and, in certain instances, can include transforming different sets of data into one coordinate system. In certain instances, registration is necessary in order to be able to compare or integrate the data obtained from these different measurements.

In this regard, optimization refers to the selection of a best element from a set of available alternatives. In a simple case, an optimization problem consists of maximizing or minimizing a real function by systematically choosing input values from within an allowed set and computing the value of the function. Generally, optimization includes finding "best available" values of some objective function given a defined domain, including a variety of different types of objective functions and different types of domains. A starting set or sets is often specified by a set of constraints, equalities or inequalities, that the members must satisfy. In some cases, the function is called an energy functional. A feasible solution that minimizes (or maximizes) the objective function is an optimal solution.

1. Cardiac Anatomy

The heart is composed of a muscular contractile organ (myocardium) surrounded by two layers of connective tissue inside and outside called endocardium and epicardium, respectively. As shown in FIG. 1, the heart has four chambers and four major valves. LV, the prominent chamber of the heart, is the major contractile chamber, and maintains the systemic circulation. Myocardial contraction is maintained by a circulatory system of coronary arteries that supplies the muscle with oxygenated hemoglobin and nutrients. Coronary arteries (right and left) are two branches of the aorta and supply the myocardium through smaller branches such as Left circumflex (LCX), Left Anterior Descending (LAD), and diagonal arteries.

Due to atherosclerosis, the coronary arteries may gradually become occluded with CAD (Coronary Artery Disease)

as the sequela. Coronary occlusion leads to disturbance in the cardiac contractile function and causes global or regional dysfunction in the heart and may be diagnosed using state-of-the-art medical imaging techniques such as echocardiography, MRI, CT, and nuclear medicine [25]. In studying ventricular motion, physicians typically assign a subjective segmental function score to different segments of the ventricles.

The blood circulation is an alternation of two phases: diastole (relaxation phase) and systole (contraction phase). Normally around 70% of the whole LV blood in end-diastole is ejected out during systole. Several indices describe the function of the heart during systole. The most important index is EF or Ejection Fraction. The ejection fraction (EF) ratio is an index of global LV function and is calculated as (EDV-ESV)/EDV, where EDV is the volume of the LV at end-diastole and ESV is the volume of the LV at end-systole. Ventricular walls thickening during systole is also a reliable index of ventricular performance—Heart failure is characterized by a significant decrease in the EF and wall thickening. An additional index of cardiac performance is myocardial mass which can be determined from myocardial volume, assuming the myocardium to have uniform density [26, 27, 28, 29].

2. Stress and Strain

Cardiac contraction and expansion is comprised of material properties such as stress and strain. These mechanical properties of the heart change in pathologic situations and, therefore, measuring the cardiac properties can act as a valuable index for diagnosis and treatment. Rather than simply measuring the displacement and forces, cardiac dynamics are better defined by stress and strain values throughout the cardiac cycle.

Figure 2:
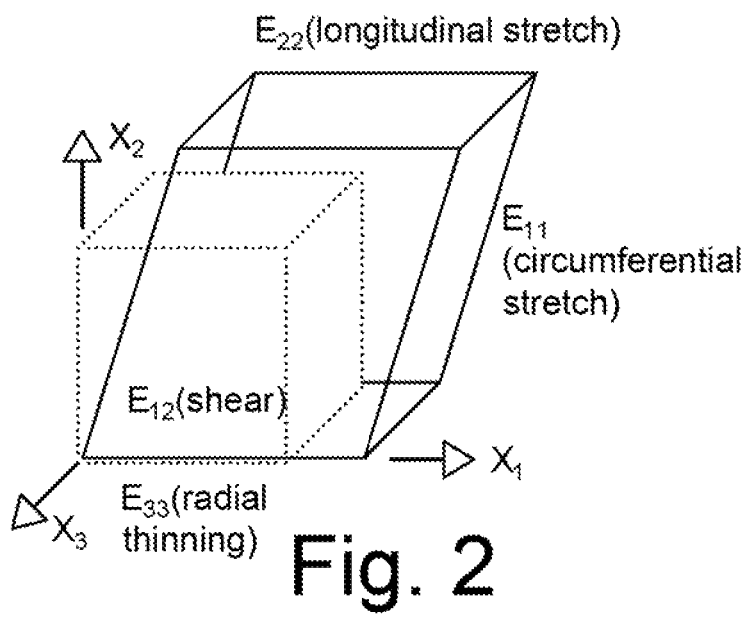
FIG. 2 is a schematic diagram showing cardiac deformation along directions $E_{11}$, $E_{12}$, $E_{22}$, and $E_{33}$.
Figure 3:
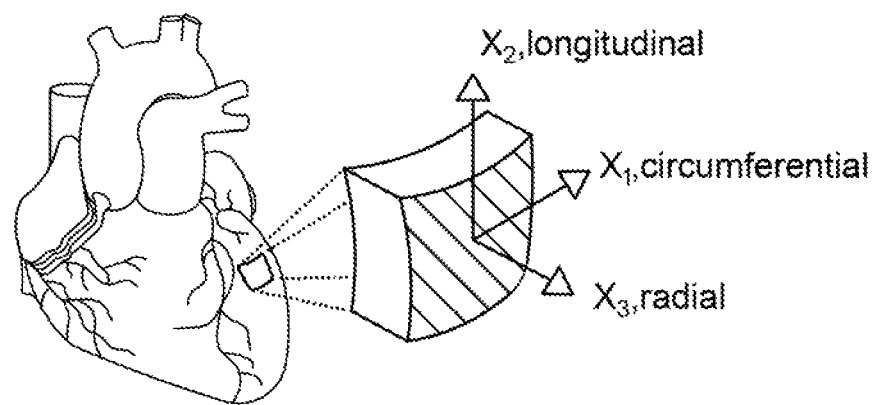
FIG. 3 is a schematic diagram showing cardiac deformation along directions $X_1$, $X_2$, and $X_3$.

Stress is defined as force per unit area, similar to the pressure. Stress is produced by active contraction and expansion of the cardiac fibers in systole and diastole and involves forces acting across surfaces between adjacent regions of muscle. Strain on the other hand is a measure of deformation of the cardiac tissue. Strain represents the change of shape at any point in the wall between the endocardium and epicardium for each point is typically calculated in an orthogonal frame of reference; e.g., radial, circumferential, and longitudinal directions. FIG. 2 and FIG. 3 show cardiac deformation along directions $E_{11}$, $E_{12}$, $E_{22}$, $E_{33}$, $X_1$, $X_2$, and $X_3$.

The stress component that is perpendicular to the cardiac surface is called normal stress, while the stress component that acts parallel to a surface is called shear stress. Normal stress changes the cardiac wall thickness, while shear stress causes an originally rectangular segment to deform into a parallelogram.

Figure 4:
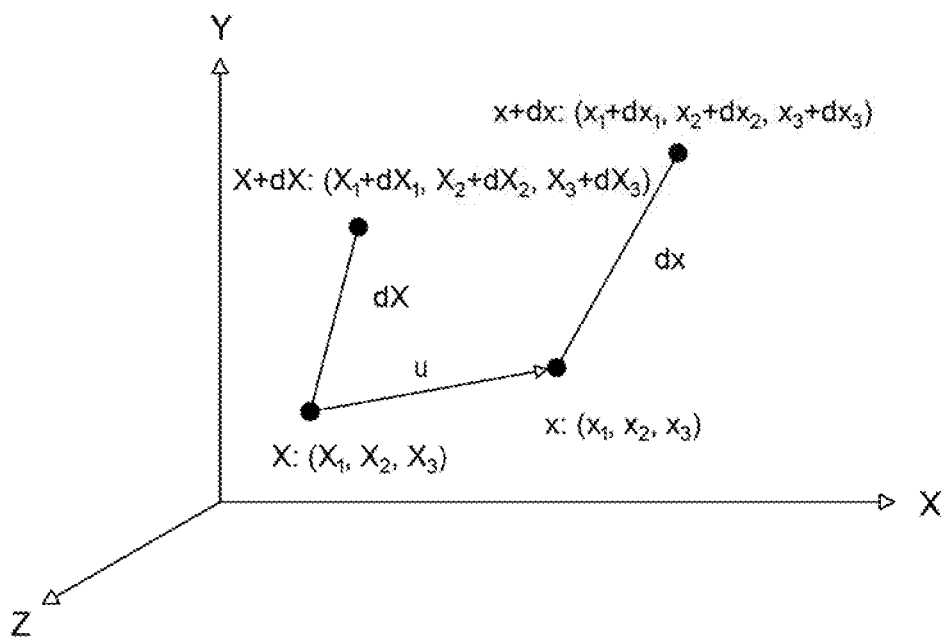
FIG. 4 is a schematic diagram showing movement of an object during deformation.

As shown in FIG. 4, if an object is at position $X=(X_1, X_2, X_3)$ prior to the deformation and is at position $x=(x_1, x_2, x_3)$ after the deformation over time (t), a mapping $x=X(X, t)$ can define the displacement. The motion (u) of the object can then be expressed as:

$$u(t)=x(t)-X \quad (1)$$

Considering the small length change (dX) at point X, then:

$$dx=\chi(X+dX)-\chi(X)\approx[\nabla\chi(X)]\cdot dX=F\cdot dX \quad (2)$$

while $\nabla$ defines a gradient operator and F shows the deformation gradient tensor of the object at X. Components of the expression in equation (2) can then be expressed as:

$$dx_i = \frac{\partial x_i}{\partial X_j} dX_j \quad (3)$$

In equation (2), deformation gradient tensor (DGT) ($F_{ij}$) is in fact nothing but:

$$F_{ij} = \frac{\partial x_i}{\partial X_j} \quad (4)$$

In matrix form, the Deformation gradient tensor (DGT) F can be expressed as:

$$F = \begin{bmatrix} F_{11} & F_{12} & F_{13} \\ F_{21} & F_{22} & F_{23} \\ F_{31} & F_{32} & F_{33} \end{bmatrix} = \begin{bmatrix} \frac{\partial x_1}{\partial X_1} & \frac{\partial x_1}{\partial X_2} & \frac{\partial x_1}{\partial X_3} \\ \frac{\partial x_2}{\partial X_1} & \frac{\partial x_2}{\partial X_2} & \frac{\partial x_2}{\partial X_3} \\ \frac{\partial x_3}{\partial X_1} & \frac{\partial x_3}{\partial X_2} & \frac{\partial x_3}{\partial X_3} \end{bmatrix} \quad (5)$$

Since $x_i=X_i+u_i$, taking required derivatives with respect to $X_1$, $X_2$, and $X_3$ in equation (5) leads to:

$$F = \begin{bmatrix} 1 & 0 & 0 \\ 0 & 1 & 0 \\ 0 & 0 & 1 \end{bmatrix} + \begin{bmatrix} \frac{\partial u_1}{\partial X_1} & \frac{\partial u_1}{\partial X_2} & \frac{\partial u_1}{\partial X_3} \\ \frac{\partial u_2}{\partial X_1} & \frac{\partial u_2}{\partial X_2} & \frac{\partial u_2}{\partial X_3} \\ \frac{\partial u_3}{\partial X_1} & \frac{\partial u_3}{\partial X_2} & \frac{\partial u_3}{\partial X_3} \end{bmatrix} \quad (6)$$

The large deflection theory definition of strain for a line segment having undeformed length dX and a deformed length dx may be arrived at as follows:

$$\epsilon = \frac{1}{2}\frac{|dx|^2-|dX|^2}{|dX|^2} = \frac{1}{2}\frac{dx^T dx - dX^T dX}{|dX|^2} = \frac{1}{2}\frac{(FdX)^T(FdX)-dX^T dX}{|dX|^2} = \frac{dX^T \frac{1}{2}(F^T F - I)dX}{|dX|^2} \quad (7)$$

Strain is a measure of deformation of the cardiac tissue. With I representing the identity matrix, the Lagrangian strain tensor at a given myocardial point and for a specific time point can be expressed as:

$$E = \frac{1}{2}(F^T F - I) \quad (8)$$

where the elements of the deformation gradient tensor, F, are $$F = \begin{pmatrix} \frac{\partial x}{\partial X} & \frac{\partial x}{\partial Y} & \frac{\partial x}{\partial Z} \\ \frac{\partial y}{\partial X} & \frac{\partial y}{\partial Y} & \frac{\partial y}{\partial Z} \\ \frac{\partial z}{\partial X} & \frac{\partial z}{\partial Y} & \frac{\partial z}{\partial Z} \end{pmatrix} \quad (9)$$

while x=X+V(X), X represents the spatial coordinates in the undeformed coordinates (typically taken to be the end-diastolic frame), and V(X) is the accumulated motion vector at the corresponding spatial location relative to the undeformed state. For the echocardiography data, the reference frame for the strain computation is considered to be the end diastolic frame and was selected based on ECG trigger. The deformation field is then computed between each two frames and is added to the motion field from the previous frame in order to measure the accumulated deformation and strain. Since the deformation fields of the consecutive frames do not represent the motion of the same pixels, spline interpolation is used to align the deformation fields. For the tagged MRI data, the end-diastolic frame is always the first acquired image which is collected immediately after the R-wave trigger.

Figure 5:
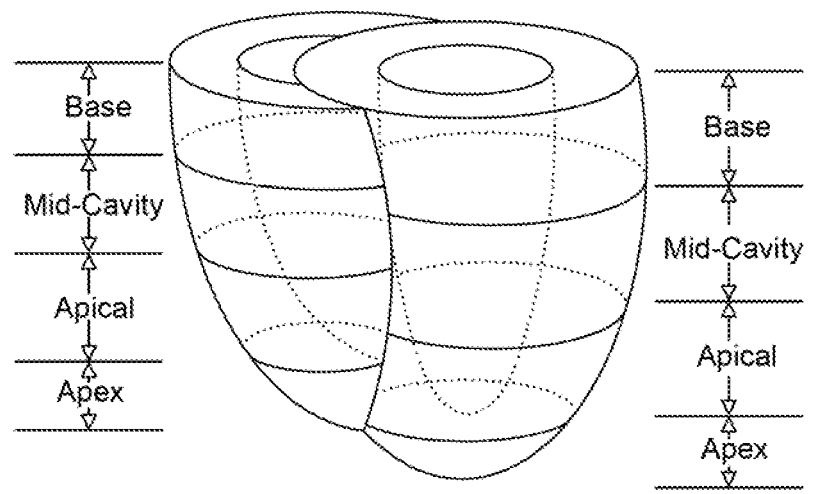
FIG. 5 is a diagram showing different cardiac regions of a left ventricle of a heart.
Figure 5:
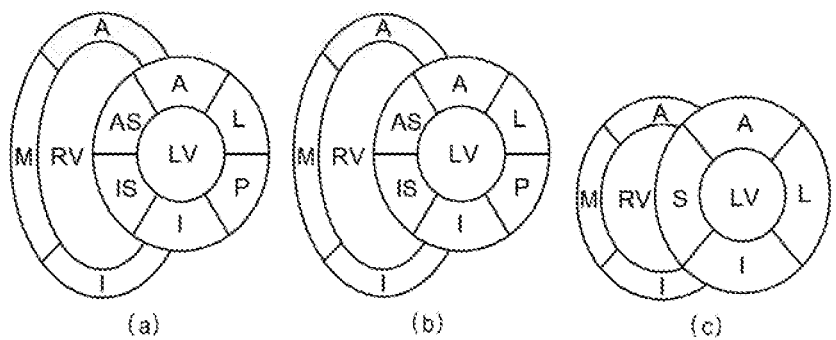

The normal Lagrangian strains in the direction of a unit vector n are calculated from the Lagrangian strain tensor through the quadratic form $n^T E n$, where n is a unit vector and can point to any 3D direction on the unit sphere. Due to the geometry of the left ventricle, the normal strains are usually calculated in radial, circumferential, and longitudinal directions. Due to extensive amount of information that is available (three quantities for each individual point), typically strains are reported on a regional basis and over time. FIG. 5 shows the different cardiac regions that are used for this purpose. The acronyms stand for antero-septal (AS), anterior (A), lateral (L), posterior (P), inferior (I), and infero-septal (IS) regions of the left ventricle.

3. A Combined B-Mode/Tissue Doppler Approach for Cardiac Motion Estimation

Displacement of the heart can be assessed using two independent techniques, namely, TDI (Tissue Doppler Imaging) and speckle tracking. TDI computes the tissue motion based on the Doppler Effect and is therefore dependent on the angle of insonification. Speckle tracking, on the other hand, involves analysis of the ultrasound B-mode or RF images. These algorithms are robust to the variation of the transducer angle but entirely rely on the properties of the echocardiographic images which may be noisy or inaccurate. The physical principles underlying B-mode and TDI are independent and therefore, can have complementary information.

Figure 6:
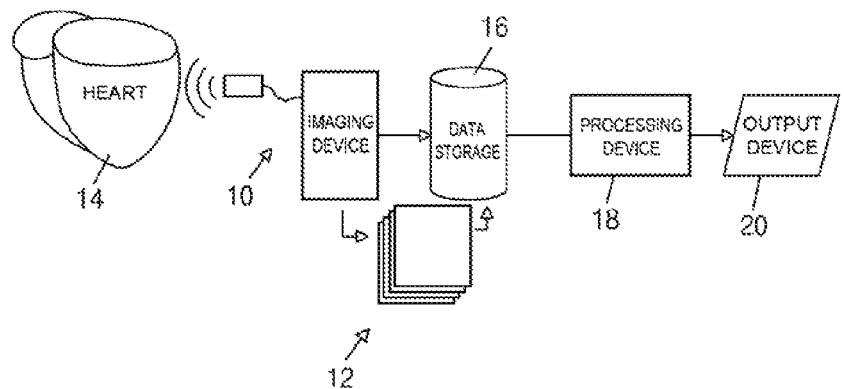
FIG. 6 is a functional block diagram of an exemplary system for cardiac motion estimation according to the invention.

FIG. 6 is a functional block diagram of an exemplary system for cardiac motion estimation according to the invention. As shown in FIG. 6, and imaging device 10 is configured to acquire a set of echocardiographic images 12 of a heart 14, the echocardiographic images including B-mode ultrasonic images and Tissue Doppler Imaging (TDI) images. Exemplary imaging devices 10 are described below. The imaging device 10 is in communication with a data storage device 16, which is configured to store the set of echocardiographic images 12. An image processing machine 18 is in communication with the data storage device 16 and is configured to calculate a motion field representing the motion of the heart 14 using the B-mode ultrasonic images and applying a velocity constraint from the TDI images, as discussed in more detail below. A output device 20, such as a video display or a printer or the like, is in communication with the image processing machine 18 and is configured to display the motion field representing the motion of the heart 14.

Figure 7:
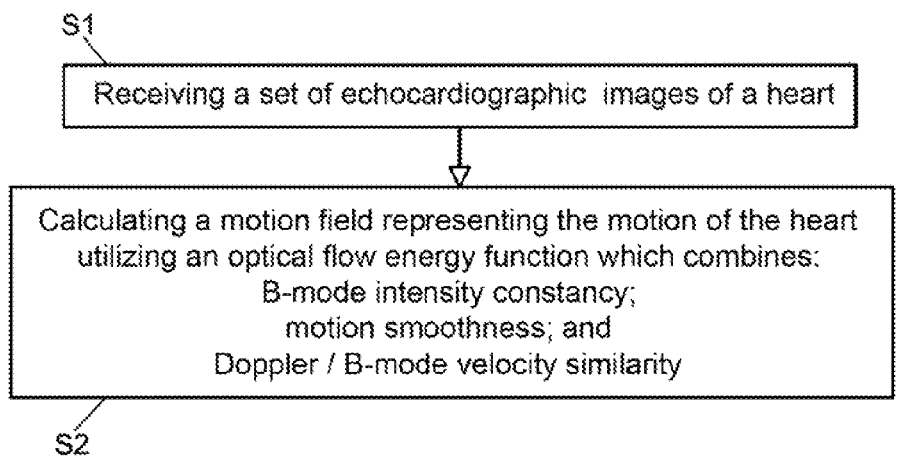
FIG. 7 shows the basic steps of an exemplary method for cardiac motion estimation according to the invention.

FIG. 7 shows the basic steps of an exemplary method for cardiac motion estimation according to the invention, including the steps of: S1 receiving, by an image processing machine, a set of echocardiographic images of the heart; and S2 calculating a motion field representing the motion of the heart utilizing an optical flow energy function which combines B-mode intensity constancy, motion smoothness, and Doppler/B-mode velocity similarity, as discussed in more detail below.

TDI and B-mode speckle tracking are different in both nature and data type. Speckle tracking is multidimensional while TDI only computes the velocity of the particle moving toward (visualized as red) or away (visualized as blue) from the transducer. This means that the computed motion is the projection of the real motion in the direction of the transducer and therefore TDI is considered angle dependent. To determine myocardial motion, the system and method of the invention utilize a new optical flow energy function (dubbed tissue Doppler imaging optical flow (TDIOF)) which combines three energy terms: B-mode intensity constancy, Doppler/B-mode velocity similarity, and motion smoothness.

1) B-mode intensity constancy: Assume that p=(x, y, t) and the flow field is w(p)=(u(p),v(p),1) where u and v are the motion vectors and x, y, and t are the spatial and temporal dimensions, B-mode intensity constancy assumes that the pixel intensity is the same along the motion vector. When I(p) is the pixel intensity at location p and I(p+w) is the pixel intensity from a subsequent frame at location p+w, then:

$$E_{data}=|I(p+w)-I(p)|^2 \quad (10)$$

Although optical flow is usually solved using calculus of variation, the recent incremental flow framework is used due to computational savings. The incremental flow assumes that an estimate of flow is already known and the best increment should be found. The intensity constancy is then changed to:

$$E_{data}=|I(p+w+dw)-I(p)|^2 \quad (11)$$

The above equation can be linearized using Taylor series expansion as shown below:

$$I_t(p+w+dw)-I(p)=I_t(p)+I_x(p)du(p)+I_y(p)dv(p) \quad (12)$$

with $$I_x(p) = \frac{\partial I(p+w)}{\partial x} \quad (13)$$

$$I_y(p) = \frac{\partial I(p+w)}{\partial y} \quad (14)$$

$$I_t(p) = I(p+w) - I(p)$$

2) Smoothness energy (i.e., motion smoothness) is defined as:

$$E_s=|\nabla(u+du)|^2+|\nabla(v+dv)|^2 \quad (15)$$

with $$|\nabla(u+du)|^2 = \left(\frac{\partial(u+du)}{\partial x}\right)^2 + \left(\frac{\partial(u+du)}{\partial y}\right)^2 \quad (16)$$

3) TDI velocity energy term (i.e., Doppler/B-mode velocity similarity): The 2D motion when projected in the direction of the transducer should be similar to the computed velocity. If $\vec{v}=(u, v)$ is the B-mode velocity and $\vec{v}_t=(u_t, v_t)$ is the transducer orientation and $w_{tdi}$ is the TDI scalar acquired from the echo machine, then the TDI energy is formulated as:

$$E_{tdi}=(\vec{v}^T\vec{v}_t-w_{tdi})^2=(u_tu+v_tv-w_{tdi})^2 \quad (17)$$

In order to keep the range of $E_{tdi}$ between 0 and 1, Geman-Mcclure penalizer is utilized:

$$\psi(s) = \frac{s^2}{s^2 + \sigma^2} \quad (18)$$

where s is the input data and $\sigma$ is the scaling parameter.

The total energy function to be minimized is then:

$$E(u,v) = E_{data} + \alpha E_s + \beta\psi(E_{tdi}) = \quad (19)$$
$$\int_\Omega (|I(P+w+dw) - I(p)|^2 + \alpha(|\nabla(u+du)|^2 + |\nabla(v+dv)|^2) +$$
$$\beta \cdot \psi((u_t(u+du) + v_t(v+dv) - w_{tdi})^2))$$

where $\alpha$ is the smoothness weight and $\beta$ is the TDI/velocity correspondence parameter (where setting $\beta$ to 0 essentially results in the Horn and Schunck optical flow frame case in the incremental flow framework). Next, u, v, du, and dv are vectorized as U, V, dU, and dV:

$$I_x = \text{diag}(I_x) \quad I_y = \text{diag}(I_y) \quad (20)$$

$D_x$ and $D_y$ are denoted as matrices related to the x and y derivative filters such that: $D_xU=u_x(x)[0-11]$. The derivative operator is used to compute the gradient of the image in each direction. In addition, the column vector $\delta_p$ is defined as a Dirac function with the only nonzero element at location p such that $\delta_p I_x = I_x(P)$. Now, the discretized version of the energy function (see (18)) becomes:

$$E = \sum_p \left(\delta_p^T(I_t + I_xdU + I_ydV)^2 + \right. \quad (21)$$
$$\alpha\left[(\delta_p^TD_x(U+dU))^2 + ((\delta_p^TD_y(U+dU))^2 + \right.$$
$$\left. (\delta_p^TD_x(V+dV))^2 + ((\delta_p^TD_y(V+dV))^2\right] +$$
$$\left. \beta((\delta^T(u_t(U+dU) + v_t(V+dV) - w_{tdi}))^2\right)$$

To minimize (20), iterative reweighted least squares is used with the stopping criterion that $$\left[\frac{\partial E}{\partial dU}; \frac{\partial E}{\partial dV}\right] = 0.$$

Here, it is noteworthy to state that since for matrix A and vectors x, b:

$$\frac{d}{dx}x^TAx = 2Ax \quad \frac{d}{dx}x^Tb = b \quad (22)$$

Therefore, $$\frac{\partial E}{\partial dU} = 2\sum_p (I_x\delta_p\delta_p^T(I_ydV + I_t) + I_x\delta_p\delta_p^TI_xdU) + \quad (23)$$
$$\alpha[(D_x^T\delta_p\delta_p^TD_x + D_y^T\delta_p\delta_p^TD_y)(U+dU)] +$$
$$\beta\psi'(E_{tdi})[u_t\delta_p(\delta_p^T((U+dU)u_t + (V+dV)v_t - w_{tdi}))] =$$
$$2((I_x^2 + \alpha L + \beta\psi'u_t^2)dU + (I_xI_y + \beta\psi'u_tv_t)dV +$$
$$(\alpha L + \beta\psi'u_t^2)U + \beta\psi'u_tv_tV + (I_xI_t - \beta\psi'u_tw_{tdi})$$

$$\frac{\partial E}{\partial dU} = 2((I_x^2 + \alpha L + \beta\psi'u_t^2)dU + (I_xI_y + \beta\psi'u_tv_t)dV + \quad (24)$$
$$(\alpha L + \beta\psi'u_t^2)U + \beta\psi'u_tv_tV + (I_xI_t - \beta\psi'u_tw_{tdi})$$

where $$L = D_x^T\psi'D_x + D_y^T\psi'D_y \quad (25)$$

$$\psi' = \text{diag}(\psi'(E_{tdi})) \quad (26)$$

and $\Sigma_p\delta_p^T$ is the identity matrix.

Similarly, $$\frac{\partial E}{\partial dV} = ((I_xI_y + \beta\psi'u_tv_t)dU + (I_y^2 + \alpha L + \beta\psi'v_t^2)dV + \quad (27)$$
$$\beta\psi'u_tv_tU + (\alpha L + \beta\psi'v_t^2)V + (I_yI_t - \beta\psi'v_tw_{tdi})$$

Finally, the following linear equation is derived as:

$$\begin{pmatrix} I_x^2\alpha L + \beta\psi'u_t^2 & I_xI_y + \beta\psi'u_tv_t \\ I_xI_y + \beta\psi'u_tv_t & I_y^2 + \alpha L + \beta\psi'v_t^2 \end{pmatrix}\begin{pmatrix} dU \\ dV \end{pmatrix} = \quad (28)$$
$$\begin{pmatrix} I_xI_t + \alpha LU - \beta\psi'u_tw_{tdi} + \beta\psi'u_t^2U + \beta\psi'u_tv_tV \\ I_yI_t + \alpha LV - \beta\psi'v_tw_{tdi} + \beta\psi'u_tv_tU + \beta\psi'v_t^2V \end{pmatrix}$$

In practice, u, v, dU, and dV are initialized as 0 with dU and dV iteratively updated using linear least squares. In order to cover a wide range of displacements and to reduce the computational time, the algorithm is applied in a multiscale strategy. The coarse scale is tackled in the first step, while the fine scale is computed in the last stage.

4. Examples

Example 1—Validation Using Simulated Computerized Phantom

Echocardiographic images are the result of the mechanical interaction between the ultrasound field and the contractile heart tissue. Previously, development and use of an ultrasound cardiac motion simulator was reported [30]. The COLE convolution based simulation technique [31] is currently utilized. The significance of an Ultrasound cardiac motion simulator is the availability of both echocardiographic images as well as the actual ground-truth vector field of deformations.

A moving 3D heart was modeled based on a pair of prolate-spheroidal representations and used for the ultrasound simulation. The 3D forward model of cardiac motion was simulated using 13 time-dependent kinematic parameters of Arts et al. [32] (see Table 2). The evolution of the 13 kinematic parameters was previously derived by Arts following a temporal fit to actual location of tantalum markers in a canine heart. In Arts' model, seven time-dependent parameters are applied to define the ventricular shape change, torsion, and shear while six parameters are used to model the rigid-body motions. To simulate the Ultrasound imaging process, scatterers were randomly distributed in the simulated LV wall and the motion prescribed by Arts' model was used to move the ultrasound scatterers. To determine Ultrasonic B-mode intensities, the COLE method was used. COLE is an efficient convolution-based method in the spatial domain, producing US simulations by convolving the segmental PSF (point spread function) with the projected amplitudes of the scatterers with the segmental PSF derived using Field II [33]-[35]. In order to model the Doppler Effect, the frequency of the RF signal was shifted in the frequency domain based on the attributed ground truth motion vector and mixed with additive Gaussian noise. If the velocity of the particle is v, ultrasound velocity is c, transducer frequency is f, and the angle between the ultrasound beam and direction of motion at a specific point is 0, then the frequency shift is:

$$\Delta f = \frac{2vf\cos\theta}{c} \quad (29)$$

The resolution of the first simulated sequence was 0.1 mm/pixel for both B-mode and TDI images and included 14 mid-ventricular temporal frames in the axial orientation. In order to analyze the robustness of the method to noise, another set of simulated images were produced by adding Gaussian noise of 1.12 db to the noise-less data.

TABLE 2

The 13 k-parameters of the Art's kinematic model for left-ventricular deformation used in our cardiac US motion simulator.

| | Non-rigid body motion |
|---|---|
| $k_1$ | Radially dependent compression |
| $k_2$ | Left ventricular torsion |
| $k_3$ | Ellipticalization in long-axis (LA) planes |
| $k_4$ | Ellipticalization in short-axis (SA) planes |
| $k_5$ | Shear in x direction |
| $k_6$ | Shear in y direction |
| $k_7$ | Shear in z direction |
| | Rigid body motion |
| $k_8$ | Rotation about x-axis |
| $k_9$ | Rotation about y-axis |
| $k_{10}$ | Rotation about z-axis |
| $K_{11}$ | Translation along x-axis |
| $K_{12}$ | Translation along y-axis |
| $k_{13}$ | Translation along z-axis |

Example 2—Validation Using Physical Cardiac Phantom

A physical cardiac phantom was built in-house, suitable for validation of echocardiographic motion estimation algorithms [36]. Here, a brief description of this phantom is provided. To manufacture the phantom, a cardiac computerized model was used to build an acrylic based cardiac mold. A 10% solution of Poly Vinyl alcohol (PVA) and 1% enamel paint were used as the basic material. PVA has the ability to mimic cardiac elasticity, ultrasound and magnetic properties. The solution was heated up to 90 deg. C. Consequently, it was poured into the cardiac mold and gradually exposed to the temperature of −20 C until it froze. The mold and the solution were kept in that temperature for 24 hours. Finally, the mold and the frozen gel were gradually exposed to the room temperature. At this point, the normal heart phantom has passed one freeze-thaw cycle.

An additional model consisting of the left and right ventricles but with a segmental thin wall in the LV was used to build an additional mold for a pathologically scarred heart. The thinner wall was designed to mimic an aneurysmal, dyskinetic wall. Three PVA-based inclusions were separately made as a circle; slab and cube using nine, six and three freeze-thaw cycles respectively. Each freeze-thaw cycle decreases the elasticity of the heart mimicking scarred myocardium. The attenuation of the PVA and speed of sound increase after each freeze-thaw cycle. The cylindrical, slab like and cube like objects were placed in the mold in different American Heart Association cardiac segments [37]. Subsequently, the PVA solution was added to fill the rest of the space in the mold. After one freeze-thaw cycle, the abnormal heart consisted of a background of normal texture with one freeze-thaw cycle plus three infarct-mimicking inclusions having 10, 7 and 4 freeze-thaw cycles. The speed of sound in PVA is 1527, 1540, 1545, and 1550 m/s and ultrasound attenuation is 0.4, 0.52, 0.57, and 0.59 db/cm for 1, 4, 7 and 10 freeze-thaw cycles. The parameters of the synthetic phantom was adjusted based on the previous phantom studies [38].

A mediastinal phantom that provides the ability to acquire trans-esophageal images was manufactured using another mold. A solution of 50% water and 50% glycerol was used to mimic the blood. Finally, a syringe was used to manually force the fluid inside and outside the phantom for contraction and expansion. The enamel paint particles are robust scatterers and can generate reliable markers on the B-mode image. Since each marker is not restricted to just one pixel, the center of the mass of each manually segmented marker is considered as landmark. The displacements of the landmarks are compared to the computed motion field for the validation purposes.

Figures 8, 9:
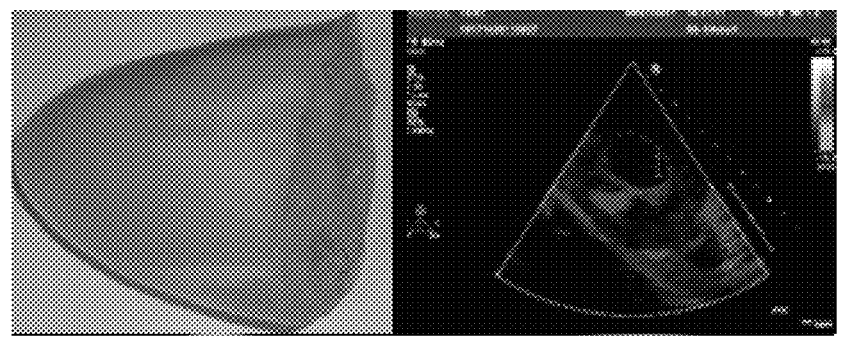
FIG. 8 is a photograph of the two-chamber model of a cardiac phantom.
FIG. 9 is a TDI image of the moving phantom during balloon inflation.

FIG. 8 is a photograph of the two-chamber model.

FIG. 9 is a TDI image of the moving phantom during balloon inflation.

Figures 10, 11:
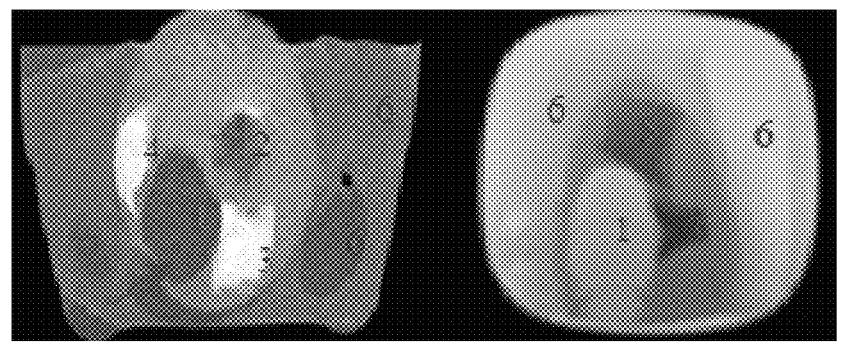
FIG. 10 is a static slice of the phantom using T1 weighted FFE.
FIG. 11 is a static slice of the phantom using balanced FFE.

FIG. 10 is a static slice of the phantom using T1 weighted FFE. The arrow points to the aneurysm (the thin ventricular wall).

FIG. 11 is a static slice of the phantom using balanced FFE (1: LV, 2: RV, 3: cylindrical inclusion, 4: slab-like inclusion, 5: cube like inclusion, 6: mediastinum and mediastinal structures).

Example 3—Patient Studies Validation: Set A: Echocardiography Studies

Two separate sets of data were utilized for in vivo validations (sets A and B). Set A contained 15 patients and was used for manual tracking validation.

Data from fifteen subjects who had already undergone echocardiographic imaging as part of their diagnostic evaluation were deidentified and transferred to the laboratory following IRB approval. The data included 13 male, 4 female, average age 52.9 (SD: 7.3). 2D echocardiography (short-axis, long-axis, four-chamber, two-chamber B-mode with TDI. At the University of Louisville Hospital's echocardiography laboratory, Echocardiographic images are acquired with a commercially available system (iE33, Philips Health Care, Best, The Netherlands) using a S5-1 transducer (3 MHz frequency) and the operator is free to change the gain and filter as needed. The full data set included two-chamber, three-chamber, four-chamber, and long-axis views.

Example 4—Patient Studies Validation: Set B: Echocardiography-MRI Studies

Set B was a joint echo and tagged MRI set and was used for both manual tracking and comparison with tagged MRI.

The prospective protocol for patient selection and imaging was approved by the Institutional Review Board of the Robley Rex Veterans' Affairs Medical Center, and a written informed consent was obtained from patients. Eight male subjects were prospectively recruited to the study with average age 54.6 (SD: 8.5). The subjects included five normal volunteers, 2 coronary artery disease (including one post myocardial infarction), and one dilated cardiomyopathy. The imaging protocol included a primary 2D echocardiography including short-axis, long-axis, three-chamber, four-chamber and two-chamber B-mode and TDI imaging as well as simultaneous B-mode/TDI imaging (two-chamber, three-chamber, four-chamber, long-axis). At the Robley Rex Veterans Affair Medical Center's echocardiography laboratory, Echocardiographic images are acquired with an iE33 commercial echocardiography system (Philips Health Care, Best, The Netherlands) using a S5-1 transducer (3 MHz frequency) and the operator is free to change the gain and filter as needed.

Following Ultrasound imaging, cine and tagged MRI data were collected in all subjects. Tagged MRI data acquisition was performed using Philips Achieva, TFE/GR sequence, TE/TR 2/4 ms, Flip Angle 15, spatial resolution 1.25×1.25 mm, slice thickness 8 mm, and spatial size 256×256×8 pixels. In all subjects, both echocardiography and MR imaging were performed within two hours to decrease any confounding events that could cause discrepancy between wall motion studies in echocardiography and MRI. MRI was performed immediately after the echocardiography. In order to ensure that the B-mode and TDI images were matched, B-mode and TDI images were simultaneously acquired. Additionally, subjects were asked to hold their breath during data collection.

Example 5—Patient Studies Validation: In-Vivo Comparison of TDIOF-Derived Strains with Strains from Tagged MRI Tagged MRI [39] is known to provide highly accurate displacement fields in the systolic portion of the cardiac cycle while the tags are present. We analyzed the strain field in echocardiography and tagged MR images of slices similar in location in the two modalities in set B. In selecting corresponding slices, qualitative anatomical landmarks such as the papillary muscles and cardiac contours as well as cine MRI images were utilized. Anatomical landmarks such as endocardial shape and papillary muscle were used to locate the appropriate short axis sections of the heart. The recently proposed SinMod (Sine wave Modeling) technique [40] was, then, used to derive displacements from tagged MRI data in the first few systolic phases of the cardiac cycle, while the tags persisted. SinMod is an automated motion estimation technique for tagged MRI that models the pixels as a moving sine wavefront. Since no pixel to pixel mapping between echo and MR images was known, the ventricular geometry from 2-D echo and tagged MRI was divided into 17 segments following the American Heart Association's recommendations. Subsequently, the averaged Lagrangian strain for each of the heart segments was compared between the two modalities. As the apex (17th segment) is difficult to visualize on short-axis MRI and B-mode images, it was excluded from the analysis. Since the frame rate of echo and MRI is not the same and the heart rate may change, it was necessary to align the images in the temporal dimension. This was done by spline interpolation of the measured strain data in the time domain.

5. Results

As noted in section 4, TDIOF was applied to three different datasets: simulated images, data collected in a physical phantom, and in vivo data (both set A and set B). To further elucidate the effect of the Doppler term, results from TDIOF were compared to Horn-Schunck (HS) optical flow and block-matching (BM), with the latter being the basis for most commercial speckle tracking methods. Since the performance of each technique depends on the parameters of the method, it was necessary to optimize the parameters. Based on simulated images, an exhaustive search was performed over the parameters of TDIOF, HS optical flow, and BM speckle tracking method (a large range was considered for each parameter) and the best values were selected experimentally. To analyze the performance of the techniques with different parameter settings, simulated images were compared to the next simulated frame after being warped using the estimated motion field. Relative mean absolute error was used for the comparison. Relative mean absolute error was computed as $$\frac{1}{N}\sum_{i,j} |(\|\hat{I}\| - \|I\|)/\|I\||;$$

where I and $\hat{I}$ are the first and subsequent warped images, and N is the total number of points.

Figure 12:
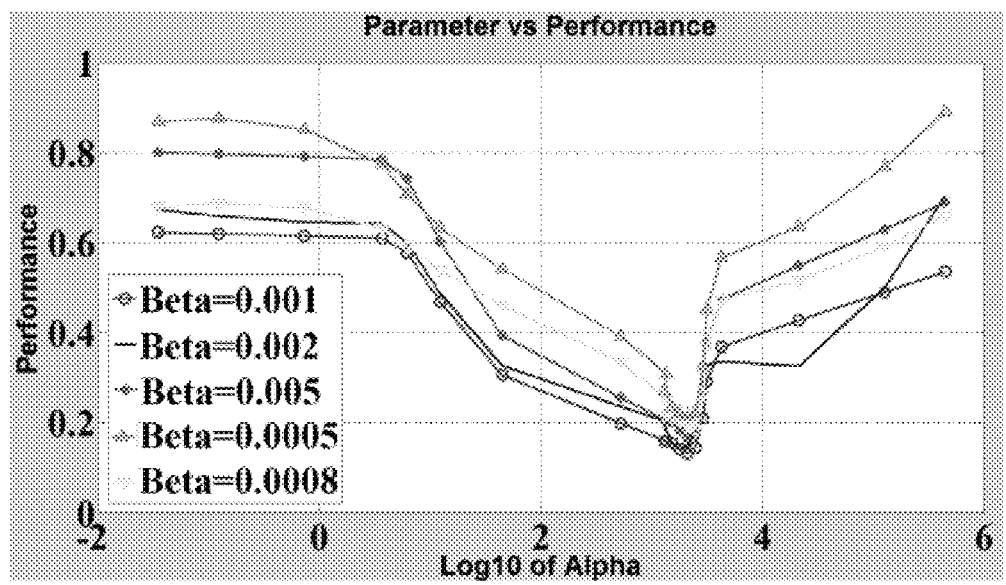
FIG. 12 is a graph of the performance of the TDIOF technique using different parameters based on relative mean absolute error.

FIG. 12 shows the performance of the TDIOF technique using different parameters based on relative mean absolute error. The X-axis is shown with a logarithmic scale in order to report a wide range of parameter settings. The performance of TDIOF is plotted versus smoothness coefficient for different TDI similarity coefficients ($\beta$). Changes of performance is evident when smoothness parameter ($\alpha$) changes. As seen from the plots, performance was more dependent on the smoothness and insensitive to the scale for the TDIOF term.

The methods were then applied to all the datasets using the resulting parameters: number of scales for multiscale implementation: 5, $\alpha$ (smoothness weight): 2000, $\beta$ (TDI similarity weight): 0.001, and $\sigma$ (penalizer parameter): 0.1. The parameters for the HS technique were set as follows: number of scales 5, and smoothness weight 2000. MATLAB 2011 was the platform for developing TDIOF using 8×3.8 GHz AMD CPU and 16 GHz RAM. The computational time for processing two frames of the in vivo echo data was 38, 25, and 51 s using BM, HS, and TDIOF, respectively.

a. Validations on Simulated Images

Figure 13:
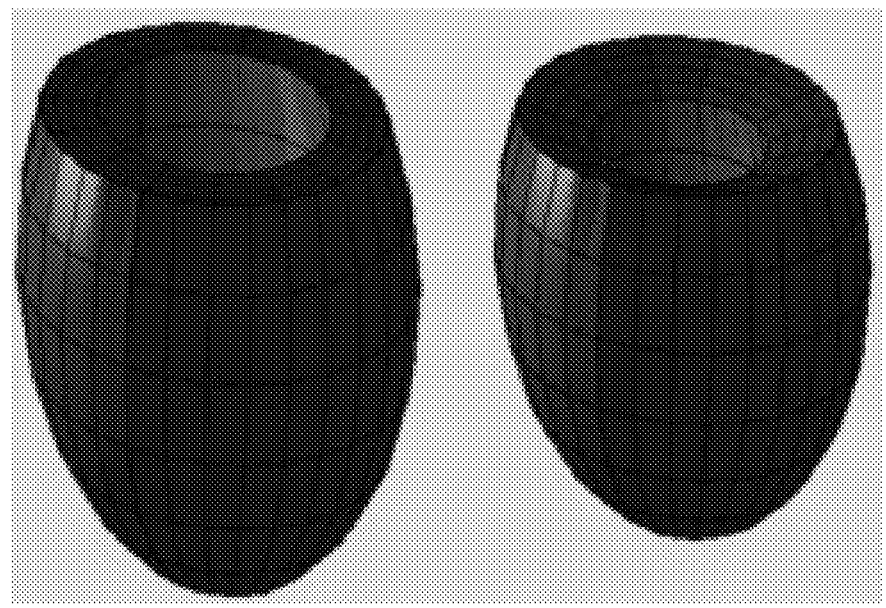
FIG. 13 is a rendering the simulated 3D cardiac model built based on Arts et al.

FIG. 13 shows the simulated 3D cardiac model built based on Arts et al. The deformation shown in the figure is that of a systolic motion.

Figure 14:
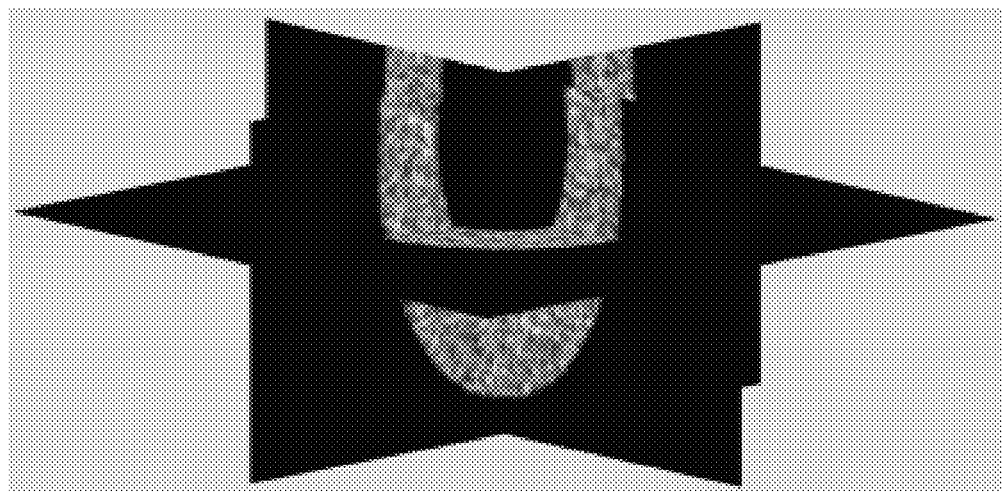
FIG. 14 is a rendering showing the 3D B-mode image deformation computed based on Arts et al.

FIG. 14 shows the 3D B-mode image deformation computed based on Arts et al.

Figure 15:
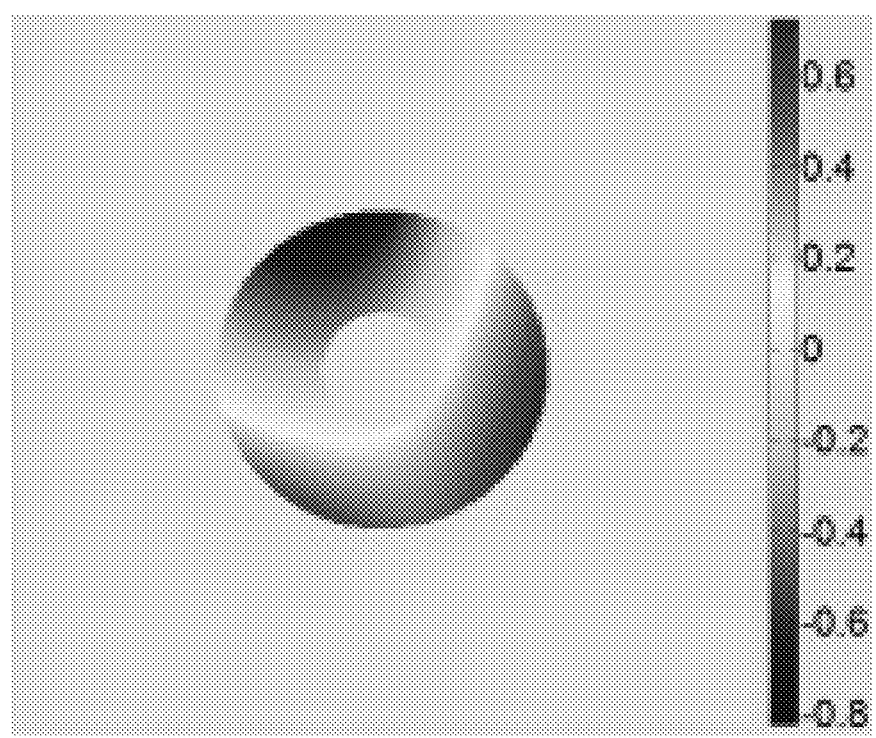
FIG. 15 is a rendering the computed TDI using the simulated sequence.

FIG. 15 shows the computed TDI using the simulated sequence—the red colors represent motion towards the transducer and the blue colors represents motion away from the transducer.

Figure 16:
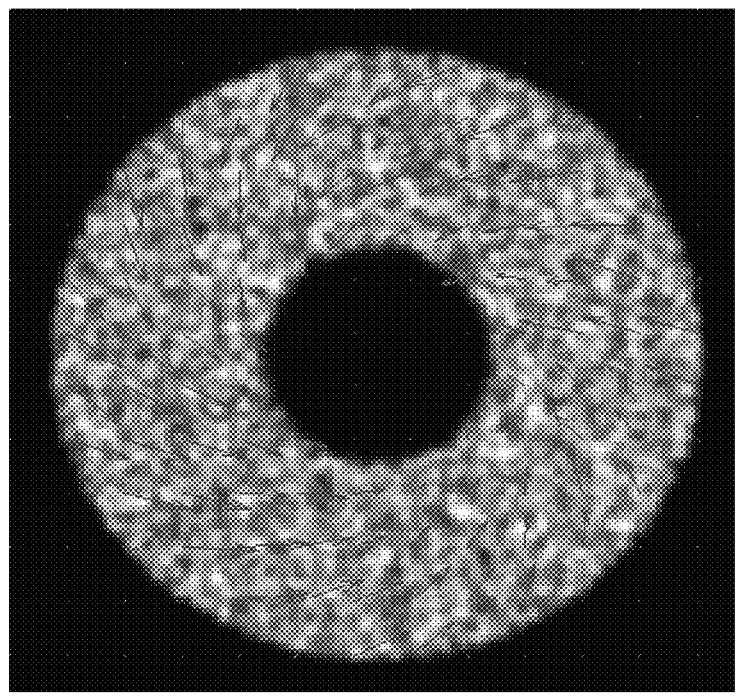
FIG. 16 is an image showing a motion field resulting from application of TDIOF to simulated data.
Figure 17:
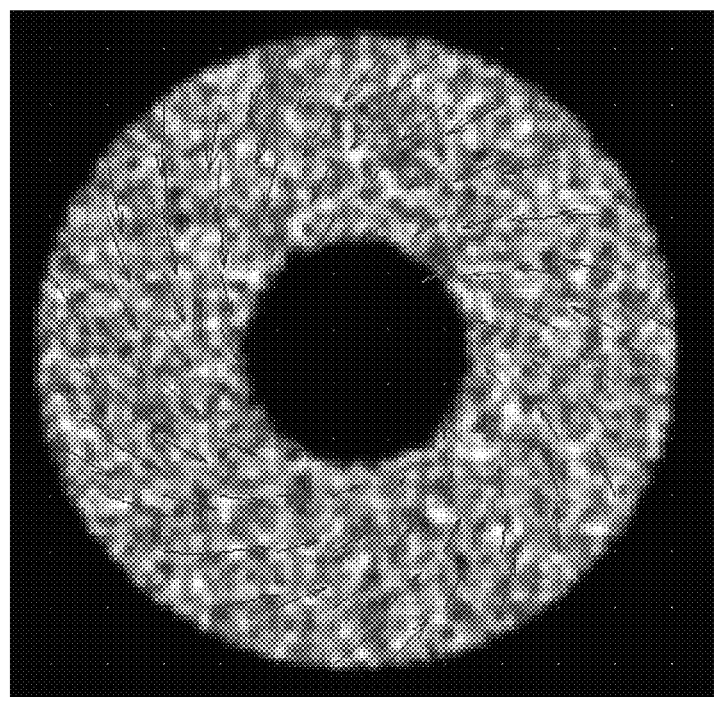
FIG. 17 is an image showing a ground truth motion field.

FIG. 16 and FIG. 17 show application of TDIOF to simulated data and comparison with ground truth. FIG. 16 shows results of TDIOF from a midventricular section of the 3D simulated echo data. FIG. 17 shows the ground truth motion field. Angular and magnitude error metrics were used for validation of the proposed technique as stated in:

$$\text{Magnitude Error} = \frac{1}{N} \sum_{i,j} \left| \frac{\|\hat{V}\| - \|V\|}{\|V\|} \right| \tag{30}$$

$$\text{Angular Error} = \frac{1}{N} \sum_{i,j} \left| \arccos \frac{\langle V, \hat{V} \rangle}{\|V\| \cdot \|\hat{V}\|} \right| \tag{31}$$

where $V$ and $\hat{V}$ are the true and estimated displacement vectors and N is the total number of vectors.

To quantitatively analyze the proposed method, averaged performance of TDIOF, Horn-Schunck optical flow, and block matching speckle tracking are reported in Table 3. The methods were applied to 14 simulated cardiac frames (one full cardiac cycle) of size 300×300×150 pixels with and without noise. The error represents the angular or magnitude error averaged over all 100 slices and over all 14 temporal frames (averaged in both space and time). Please note that TDIOF was applied to 100 short-axis cross sections of the simulated heart. Table 3 illustrates that TDIOF has markedly improved performance on noisy images.

Figure 18:
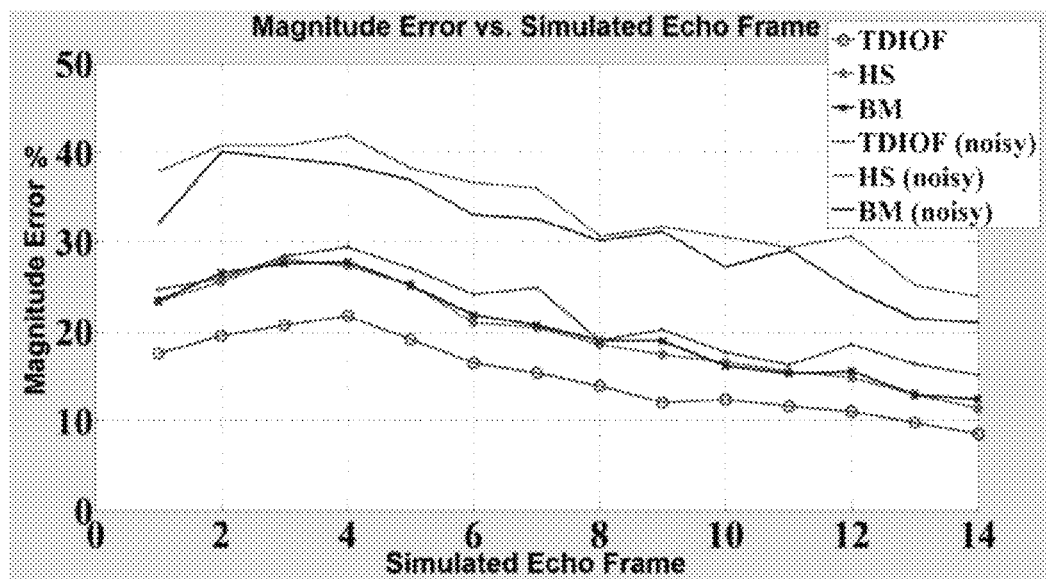
FIG. 18 is a graph showing the magnitude error over one cardiac cycle for three techniques.
Figure 19:
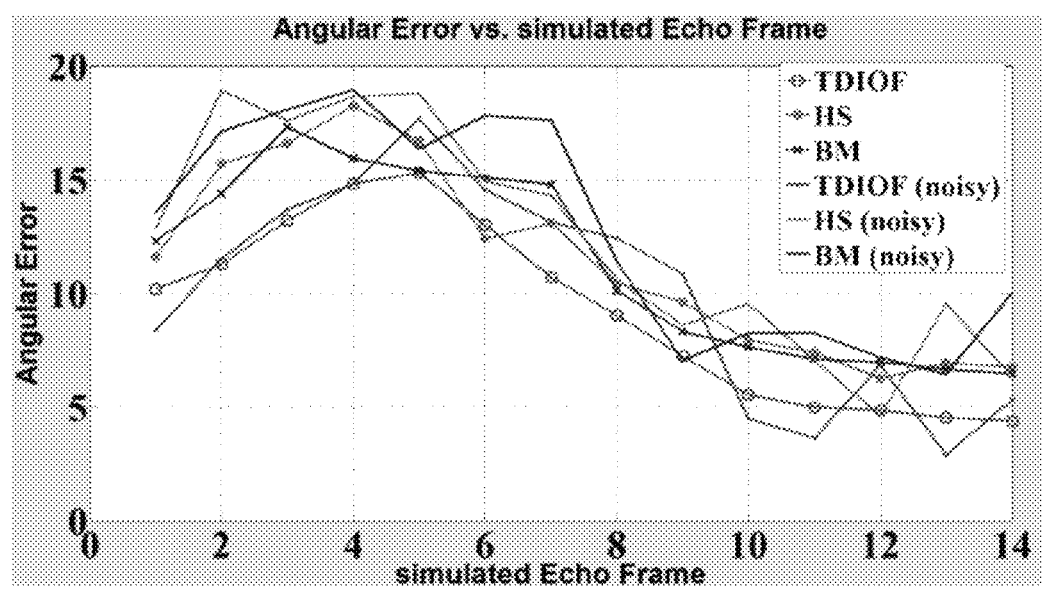
FIG. 19 is a graph showing the angular error over one cardiac cycle for three techniques.

FIG. 18 shows the magnitude error and FIG. 19 shows the angular error over one cardiac cycle for the three techniques—note that for each time point, the errors have been averaged over all spatial positions and all slices. It is evident that for all methods the errors are more pronounced in systolic frames compared to diastolic frames. This is believed to be due to larger out of plane displacements causing errors for the 2-D method.

From FIG. 18 and FIG. 19, it can also be observed that, TDIOF outperforms Horn-Schunck optical flow and BM speckle tracking more significantly on noisy images.

b. Validations on Data Collected in a Physical Phantom

In order to validate TDIOF on phantom data, the enamel markers on the B-mode images were manually segmented and the centers of mass of the markers were considered as landmarks. The error was computed on 128 landmarks over one cardiac cycle with 54 2D echocardiographic frames. As with simulated images, angular and magnitude errors were used to analyze the performance. The averaged magnitude and angular error of the landmarks for TDIOF, HS optical flow, and BM speckle tracking are shown in Table 4.

TABLE 4

Comparison of performance of TDIOF with HS optical flow and BM speckle tracking on physical phantom data.

| Data | Phantom (slow heart rate) | | | Phantom (fast heart rate) | | |
|---|---|---|---|---|---|---|
| Method | TDIOF | HS | BM | TDIOF | HS | BM |
| Magnitude Error (pixel/frame) | 0.22 ± 0.13 | 0.37 ± 0.19 | 0.32 ± 0.17 | 0.35 ± 0.15 | 0.49 ± 0.21 | 0.47 ± 0.22 |
| Angular Error (Degrees/frame) | 15.2 ± 4.7 | 29.0 ± 9.7 | 27.3 ± 9.4 | 26.5 ± 9.8 | 47.6 ± 12.1 | 42.0 ± 11.6 |

BM: Block-Matching, HS: Horn-Schunck

Figure 20:
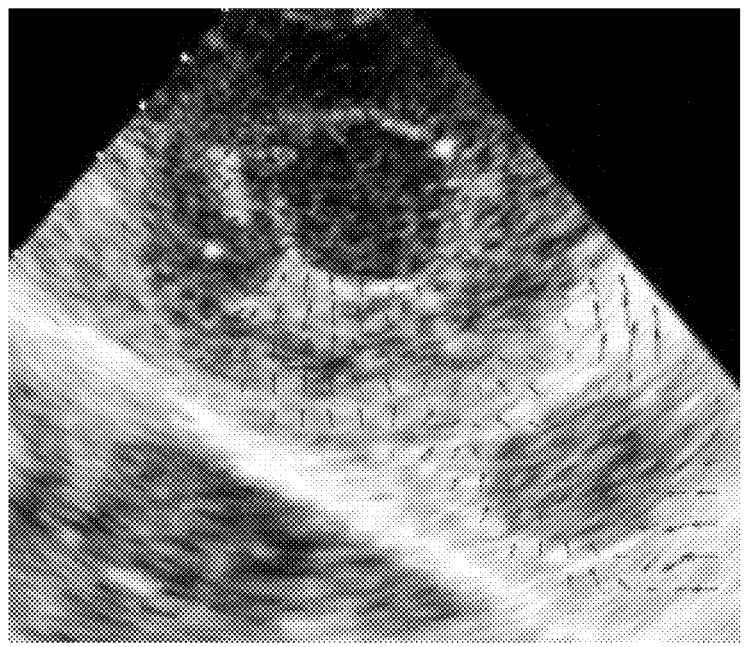
FIG. 20 is an image showing application of TDIOF applied to the physical phantom in "systole."

FIG. 20 shows application of TDIOF applied to the physical phantom in "systole."

Figure 21:
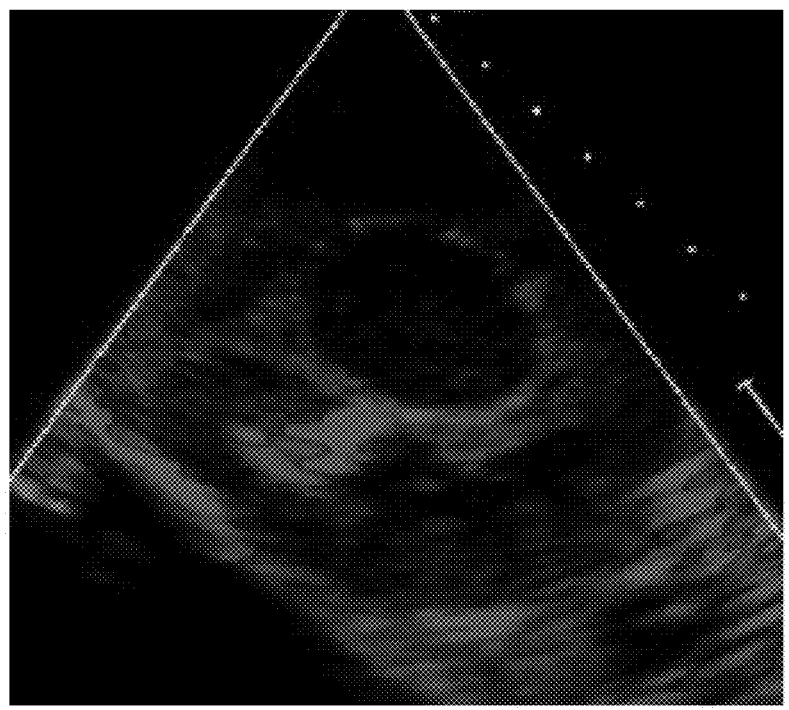
FIG. 21 is an image showing application of TDI applied to the physical phantom in "systole."

FIG. 21 shows application of TDI to the physical phantom in "systole."

c. Validations on In Vivo Images

The algorithm was also evaluated in a similar way using in vivo images with 519 landmarks selected by an expert over 106 sets acquired from 23 patients. Landmarks were prominent regions in in vivo images such as speckles that could easily be detected. Each landmark was delineated and the center of mass of the landmark was defined to be the actual location. The average error for each of the three methods (TDIOF, Horn-Schunck, block matching) applied to in vivo data was classified per segment and is reported in Table 5.

TABLE 3

TDIOF vs. HS optical flow and BM speckle tracking when applied to simulated images

| Data | Simulation (no noise) | | | Simulation (SNR 1.12 db) | | |
|---|---|---|---|---|---|---|
| Method | TDIOF | HS | BM | TDIOF | HS | BM |
| Magnitude Error (pixel/frame) | 0.15 ± 0.09 | 0.20 ± 0.13 | 0.20 ± 0.14 | 0.22 ± 0.12 | 0.34 ± 0.16 | 0.31 ± 0.15 |
| Angular Error (Degrees/frame) | 9.2 ± 3.8 | 11.2 ± 5.2 | 11.3 ± 5.6 | 10.0 ± 5.5 | 12.5 ± 6.8 | 12.7 ± 6.0 |

BM: Block-Matching, HS: Horn-Schunck

TABLE 5

Comparison of displacement errors for TDIOF, HS optical flow, and BM speckle tracking on 17 AHA segments averaged over 23 patient data sets. (antero-septal (AS), anterior (ANT), Lateral (LAT), infero-lateral (IL), infero-lateral (IL), inferior (INF), and infero-septal (IS))

| Method | | Apical-ANT | Apical-LAT | Apical-INF | Apical-septal | Mid-Ant | Mid-AL | Mid-IL | Mid-INF |
|---|---|---|---|---|---|---|---|---|---|
| Magnitude | TDIOF | 0.25 ± 0.09 | 0.23 ± 0.09 | 0.25 ± 0.10 | 0.26 ± 0.10 | 0.18 ± 0.07 | 0.19 ± 0.06 | 0.19 ± 0.06 | 0.17 ± 0.07 |
| Error | HS | 0.40 ± 0.14 | 0.39 ± 0.12 | 0.44 ± 0.16 | 0.41 ± 0.14 | 0.36 ± 0.13 | 0.36 ± 0.14 | 0.34 ± 0.13 | 0.37 ± 0.12 |
| (pixel/frame) | BM | 0.37 ± 0.14 | 0.35 ± 0.13 | 0.43 ± 0.14 | 0.40 ± 0.14 | 0.32 ± 0.14 | 0.34 ± 0.11 | 0.33 ± 0.09 | 0.32 ± 0.14 |
| Angular | TDIOF | 22.7 ± 0.09 | 27.5 ± 0.10 | 25.4 ± 0.09 | 23.5 ± 0.08 | 17.7 ± 0.08 | 16.3 ± 0.07 | 19.0 ± 0.08 | 20.1 ± 0.08 |
| Error | HS | 34.2 ± 0.11 | 35.5 ± 0.13 | 39.1 ± 0.12 | 41.7 ± 0.14 | 32.4 ± 0.09 | 31.6 ± 0.08 | 32.0 ± 0.14 | 35.4 ± 0.09 |
| (degrees/frame) | BM | 26.5 ± 0.09 | 25.7 ± 0.09 | 24.5 ± 0.10 | 27.5 ± 0.09 | 23.8 ± 0.10 | 29.2 ± 0.14 | 25.9 ± 0.10 | 24.0 ± 0.09 |

| Method | | Mid-IS | Mid-AS | basal-Ant | basal-IL | basal-IL | basal-INF | basal-IS | basal-AS | Apex |
|---|---|---|---|---|---|---|---|---|---|---|
| Magnitude | TDIOF | 0.20 ± 0.08 | 0.17 ± 0.07 | 0.25 ± 0.09 | 0.24 ± 0.10 | 0.23 ± 0.10 | 0.28 ± 0.09 | 0.24 ± 0.10 | 0.26 ± 0.09 | 0.61 ± 0.19 |
| Error | HS | 0.35 ± 0.14 | 0.33 ± 0.11 | 0.41 ± 0.14 | 0.39 ± 0.12 | 0.42 ± 0.14 | 0.43 ± 0.10 | 0.44 ± 0.11 | 0.46 ± 0.15 | 0.78 ± 0.22 |
| (pixel/frame) | BM | 0.33 ± 0.12 | 0.34 ± 0.13 | 0.37 ± 0.12 | 0.38 ± 0.09 | 0.40 ± 0.14 | 0.41 ± 0.10 | 0.44 ± 0.14 | 0.40 ± 0.13 | 0.72 ± 0.25 |
| Angular | TDIOF | 19.3 ± 0.09 | 17.8 ± 0.08 | 23.5 ± 0.10 | 21.8 ± 0.08 | 26.7 ± 0.10 | 28.7 ± 0.11 | 24.5 ± 0.08 | 23.2 ± 0.09 | 52.9 ± 0.23 |
| Error | HS | 37.3 ± 0.14 | 31.0 ± 0.13 | 37.8 ± 0.12 | 39.5 ± 0.14 | 32.6 ± 0.13 | 35.4 ± 0.10 | 33.7 ± 0.09 | 37.1 ± 0.14 | 58.6 ± 0.21 |
| (degrees/frame) | BM | 24.8 ± 0.10 | 26.5 ± 0.08 | 27.2 ± 0.09 | 29.3 ± 0.11 | 29.7 ± 0.14 | 31.5 ± 0.12 | 29.1 ± 0.09 | 34.0 ± 0.14 | 56.6 ± 0.22 |

Figure 22:
FIG. 22 is an image showing the application of the TDIOF technique to four-chamber B-mode data during diastole.

FIG. 22 shows the application of the TDIOF technique to four-chamber B-mode data during diastole. As expected, TDIOF-derived displacements are larger for the basal segments when compared to the apical segments.

d. Comparison of Strains from TDIOF and Tagged MRI

In this part of the study, radial and circumferential strains derived from TDIOF, HS optical flow, and BM speckle tracking were computed from B-mode echo and were compared to tagged MRI strains. Anatomical landmarks such as endocardial shape and papillary muscle locations were used to locate the corresponding short axis sections of the heart in tagged MRI and echocardiography. In addition, since the papillary muscles could not be easily visualized in the tagged studies, non-tagged cine MR images were used to better define the papillary muscles locations. Despite these efforts to ensure correspondence of the data, as alignment of the data based on landmarks could only be approximate (due to differences in slice thickness and identical view orientation in echo and MRI), and the results reported here should only be qualitatively interpreted.

The image-derived strain values related to the same cardiac phase and the same sections of the same patient were compared by averaging the corresponding radial and circumferential strain values for each of the 17 AHA segments. For alignment, the short-axis tagged MR images were visually matched to the corresponding short axis echocardiographic images acquired from basal, mid-ventricular, and apical slices. Since the tag lines fade after systole, only the first 3-4 systolic tagged frames and the corresponding temporal extent in echo were considered in this analysis. Furthermore, since the number of the frames in echocardiography is several times that of tagged MRI data (roughly 20 tagged MR frames vs. 4 echocardiographic frames during the cardiac cycle), the strain fields in echo images were interpolated using spline interpolation to match the systolic tagged MRI frames. Finally, 2-D strain maps from corresponding echocardiography and tagged MRI were computed and averaged over 17 segments.

FIG. 23 shows B-mode and TDI images in early systole at the high papillary muscle level of a subject.

FIG. 24 shows the computed motion of the heart between these two frames using the Horn-Schunck optical motion field.

FIG. 25 shows the computed motion of the heart between these two frames using the TDIOF motion field.

FIG. 26 shows the tagged MRI motion field for the same approximate slice location in systole.

Figure 27:
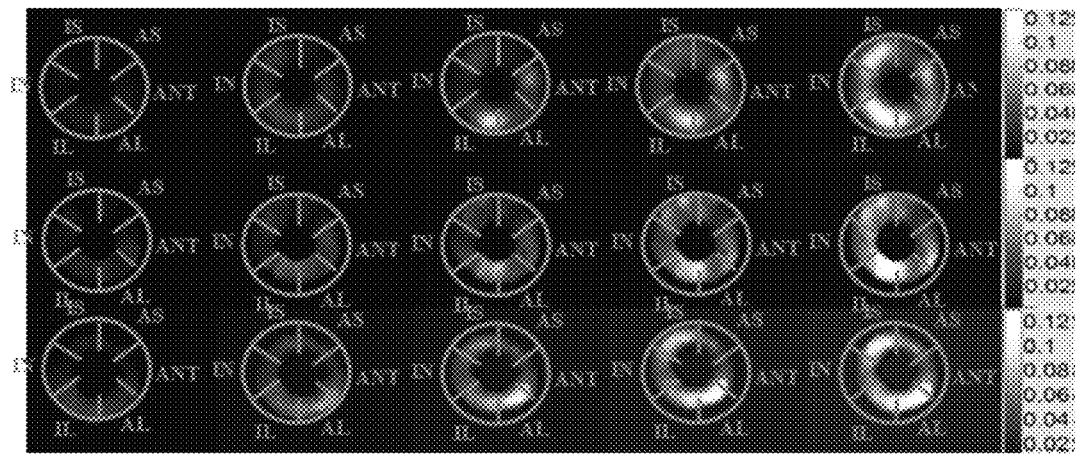
FIG. 27 and FIG. 28 are images showing the cardiac strain maps for the same cardiac phase and same slice.
Figure 28:
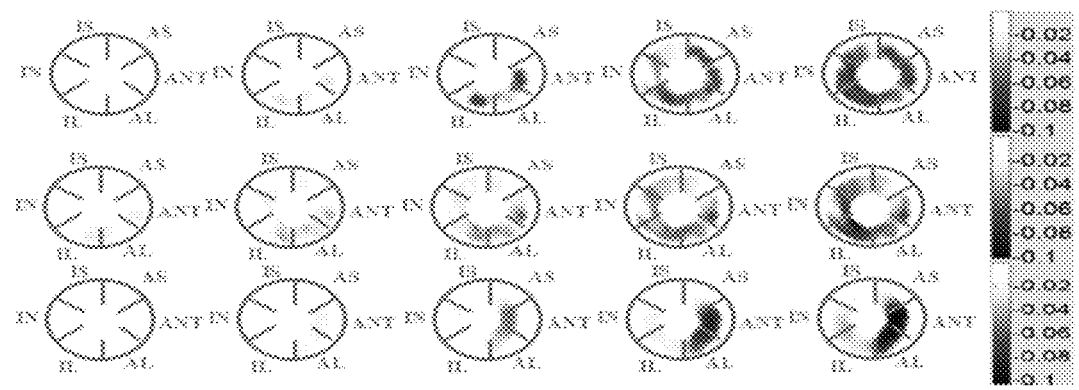

FIG. 27 and FIG. 28 show the cardiac strain maps for the same cardiac phase and same slice.

FIG. 27 compares the radial strain map with the tagged MRI radial strain map. The top row are Lagrangian radial strain maps computed from BM. The middle row are Lagrangian radial strain maps computed from TDIOF. The lower row are Lagrangian radial strain maps computed with SinMod from tagged MRI during the same cardiac phase at the high papillary muscle level in one subject. The tagged MR images are resized to match the echo images with respect to the size. As expected and observed from the tagged MRI results, the radial strains from TDIOF are positive and gradually increase during systole. The increased radial strain is more pronounced in AL and IL segments in both SinMod derived and TDIOF strain maps. The increased radial strain is also prominent in the AS and IS segments.

FIG. 28 shows the circumferential strain map compared to the tagged MRI circumferential strain map. The top row are Lagrangian circumferential strain maps computed from BM. The middle row are Lagrangian circumferential strain maps computed from TDIOF. The lower row are Lagrangian circumferential strain maps computed with SinMod from tagged MRI during the same cardiac phase at the high papillary muscle level in one subject. The tagged MR images have been resized to match the echo images with respect to size. As expected and observed from the tagged MRI results, the circumferential strains from TDIOF are negative and gradually increase in magnitude during systole. This increase is more pronounced in AL and ANT segments in both SinMod tagged MRI-derived and TDIOF strain maps.

Figure 29:
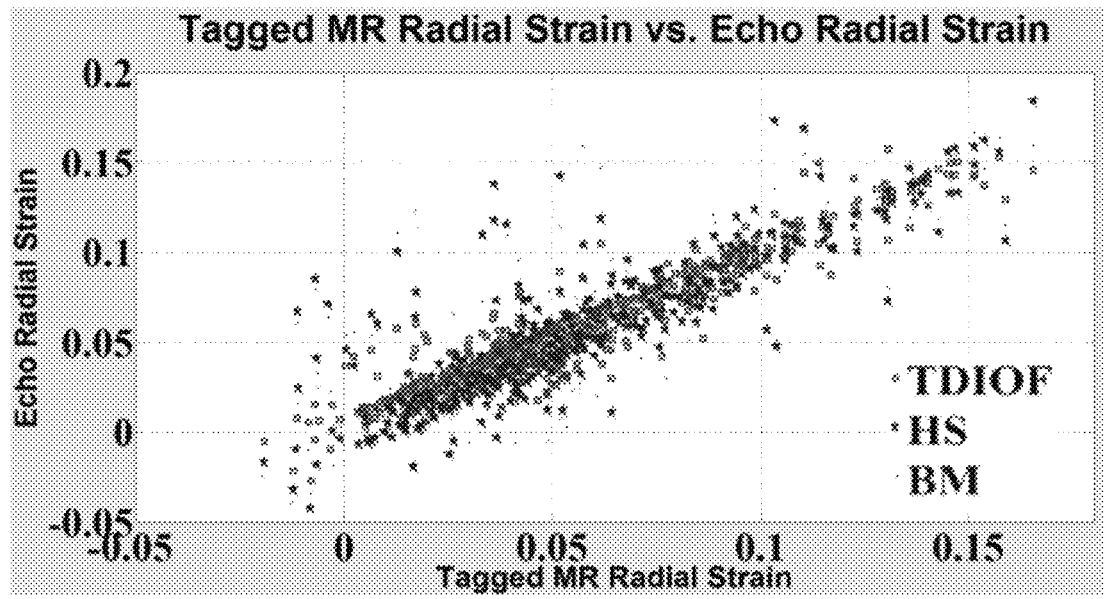
FIG. 29 is a graph showing correlation studies of the radial strain values compared to tagged MRI.
Figure 30:
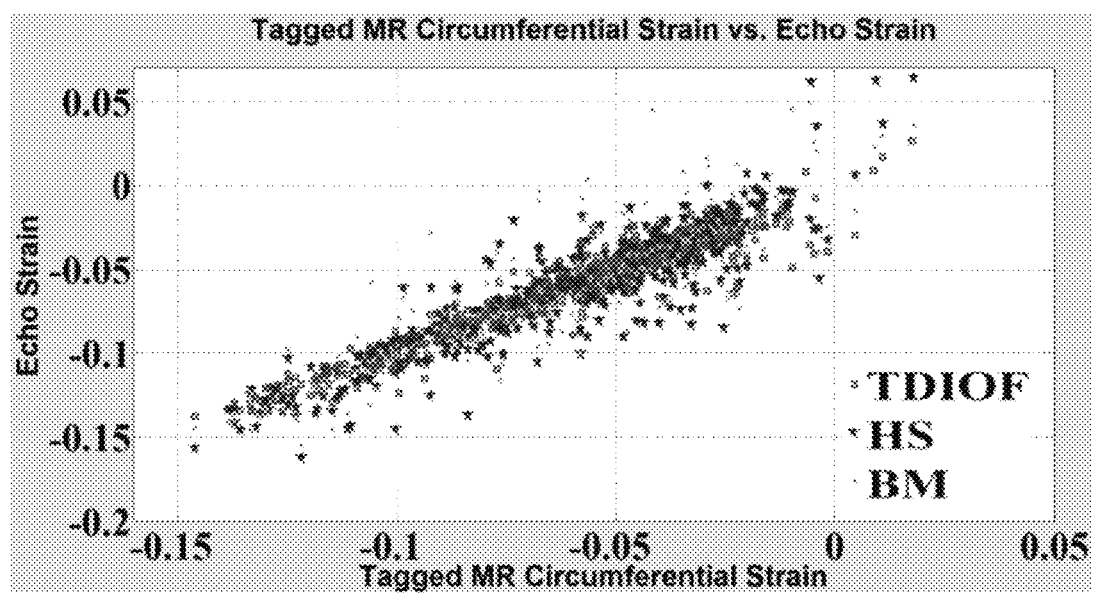
FIG. 30 is a graph showing correlation studies of the circumferential strain values compared to tagged MRI.

To compare the performance of TDIOF and HS, statistical analysis of the strain map results are helpful. FIG. 29 shows correlation studies of the radial strain values compared to tagged MRI, and FIG. 30 shows correlation studies of the circumferential strain values compared to tagged MRI. For both cases, it is evident that the HS strain values are more scattered compared to the tagged strain values. The plots include corresponding average strain quantities for 17 segments in eight patients over four tagged MRI frames. The correlation coefficient (r) for the TDIOF radial strain values compared to the tagged MRI radial strain values was 0.83 (P<0.001), while the correlation coefficient (r) for the HS and BM radial strain values compared to the tagged MRI radial strain values was 0.71 (P<0.001) and 0.75 (P<0.001), respectively. The correlation coefficient (r) for the TDIOF circumferential strain values compared to the tagged MRI circumferential strain values was 0.86 (P<0.001), while the correlation coefficient (r) for the HS and BM circumferential strain values compared to the tagged MRI circumferential strain values was 0.77 (P<0.001) and 0.79 (P<0.001). Since apex is excluded, there are 16 (segments)×8 (patients)×4 (tagged MRI frames)=512 points for each technique. Therefore, it may be concluded that for both radial and circumferential strains, TDIOF analysis achieves a more significant correlation with the tagged MRI in comparison to HS and BM analysis. This effect is believed to be due to the additional Doppler term that is added to the TDIOF framework. The comparison of TDIOF and HS radial strain using student t-test showed superiority of TDIOF (95% confidence interval, P<0.001). Similarly, the comparison of TDIOF and HS circumferential strain using student t-test showed superiority of TDIOF (95% confidence interval, P<0.001). The comparison of TDIOF and BM radial strain using student t-test was statistically meaningful (95% confidence interval, P<0.001). The comparison of TDIOF and BM circumferential strain using student t-test was prominent as well (95% confidence interval, P<0.001).

e. In Vivo Comparison of TDIOF-Derived Strains with Strains from iE33 Q-Lab

Ten patients of the dataset were analyzed using both TDIOF and Philips iE 33 Q-lab speckle tracking methods. The strain values were averaged for each longitudinal four-chamber and three-chamber cardiac segment. Averaged cardiac strain values derived from TDIOF were compared to the strain values derived from iE33 STE. However, iE 33 Q-lab techniques are based on B-mode images and, theoretically, cannot produce TDIOF results. Therefore, iE 33 strain values cannot be considered ground truth for this technique but may illustrate how combined B-mode/TDI correlates with pure B-mode motion estimation.

Figures 31, 32:
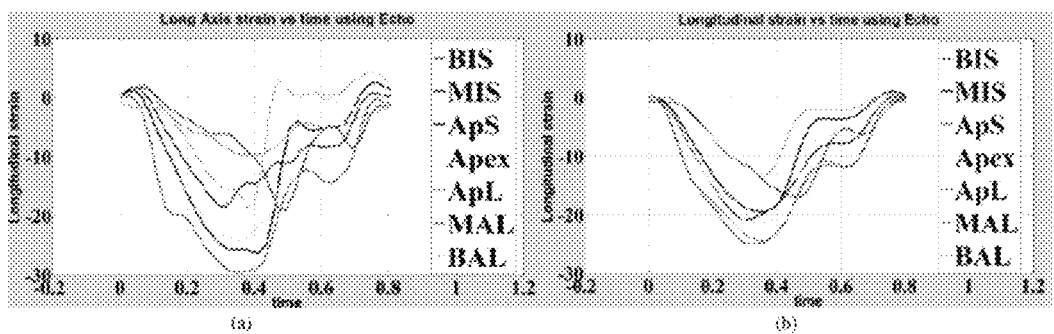
FIG. 31 is a graph showing strain curves for different long-axis cardiac segments using iE 33 STE in a patient in set A (normal echocardiography and normal cardiac nuclear scan).
FIG. 32 is a graph showing strain curves for different long-axis cardiac segments using the fusion technique (i.e., the averaged segmental strain curved derived from iE 33 and TDIOF) in the same patient.

FIG. 31 shows strain curves for different long-axis cardiac segments using iE 33 STE in a patient in set A (normal echocardiography and normal cardiac nuclear scan).

FIG. 32 shows strain curves for different long-axis cardiac segments using the fusion technique (i.e., the averaged segmental strain curved derived from iE 33 and TDIOF) in the same patient. The correlation between the TDIOF strains and iE 33 Q-lab strain values showed a high degree of correlation between the two methods.

Figure 33:
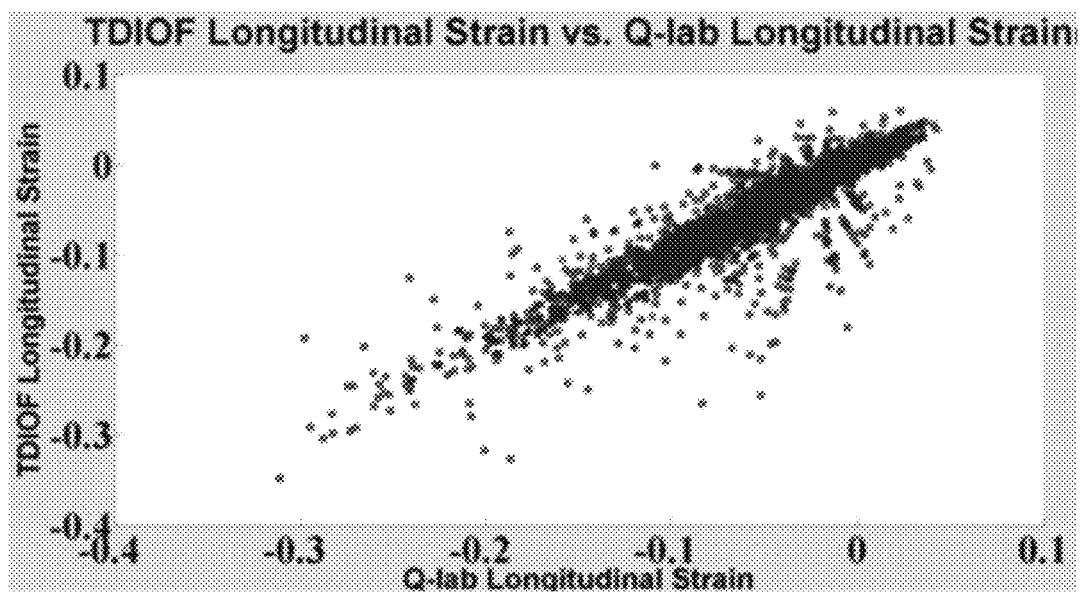
FIG. 33 is a graph showing the correlation value of the in vivo longitudinal strain derived from the TDIOF fusion method with echo-machine derived strain in ten patients imaged in four-chamber and three-chamber views.

FIG. 33 shows the correlation value of the in vivo longitudinal strain derived from the TDIOF fusion method with echo-machine derived strain in ten patients imaged in four-chamber and three-chamber views. The correlation of the results using the fusion method was 0.76 (P<0.001) compared to the STE.

6. Discussion

Improved clinical diagnosis and therapy of CVDs rely on novel techniques for measuring the regional myocardial function. Increased accuracy, even in the range of 15-20%, as has been demonstrated herein, has the potential to lead to more accurate strain values and earlier diagnosis and therapy. Early diagnosis and treatment of heart disease is indeed crucial for reduction of morbidity as well as mortality associated with CVD.

In order to increase the accuracy of motion estimation and speckle tracking techniques and to overcome the angle dependency of TDI, fusion of the techniques has been described. TDIOF makes use of the combination of B-mode and Doppler energy terms, minimized using linear algebraic methods. To show the superiority of TDIOF, two approaches to validation were utilized.

1) Manual tracking by an expert in echocardiography images: The proposed method has less averaged error in different cardiac segments as shown in Table 5. Depending on the cardiac segment, it was shown that TDIOF increased the accuracy of motion estimation by 15-20%.

2) Correlation with tagged MRI: In order to compare the similarity between the two modalities, in a correlative patient study, the proposed technique was quantitatively compared to tagged MRI. It was shown that in comparison to HS and BM methods, TDIOF correlated more significantly with tagged MRI (see FIG. 29 and FIG. 30). Although this application demonstrates that the additional Doppler term is able to increase the accuracy of the intensity (B-mode)-based methods in tracking the left-ventricular wall motion, the additional Doppler term may very well be added to other cardiac ultrasound image registration techniques and a corresponding improvement in performance is expected. As demonstrated in the simulation study, the improvement in performance is more pronounced on noisy images. TDI and B-mode contribute to each other in the presence of noise in the TDIOF framework. While the B-mode image is noisy and incoherent compared to the general cardiac motion, Doppler data drive the motion vectors more effectively. Contrarily, when TDI is noisy, B-mode-based motion is coherent with the rest of the cardiac motion and is more prominent.

TDIOF had better performance when compared to HS and Block matching in simulated, phantom, and in vivo data. Due to increased thickness of the wall, the results were better in mid-ventricular slices for all three methods. Nevertheless, results at the basal and apical slices were still acceptable. Due to poor acquisition at the apex, results for apical segments, were not as good for all three techniques compared. Similarly, in comparison to HS and BM, results from TDIOF correlated more significantly with tagged MRI. It is evident from FIG. 27 and FIG. 28 that both radial and circumferential strains increase over the cardiac systole, while the heart is contracting and peaks at end systole and then as the heart recoils back to the original length the cardiac strain decreases to about zero at end diastole. It should be noted that the strain values for TDIOF and tagged MRI are not exactly the same because it is not possible to perfectly align the images in space and time due to differences in image slice thickness, resolution, and precise image orientation.

a. Comparison with Previous Work

A comparison of correlative strain results for TDIOF reported in this paper can further illustrate the performance of the proposed technique. In [41], a comparison of MRI-derived strains and speckle tracking-derived strains were reported. The inventors collected data in patients using a commercially available system (Vivid 7, GE Vingmed Ultrasound AS, Horten, Norway) and performed off-line analysis (EchoPac BT04, GE Vingmed Ultrasound AS). Subsequently, the same group of patients underwent tagged MRI scan and HARP off-line analysis to determine the regional strains. The correlation between radial strain based on B-mode speckle tracking and tagged MRI was reported to be (r=0.60, p<0.001) while the correlation between circumferential and longitudinal strain values based on B-mode speckle tracking and tagged MRI was reported to be (r=0.51, p<0.001) and (r=0.64, p<0.001). The inventors concluded that there is a modest correlation between echocardiographic and tagged-MRI-derived strains.

b. Limitations

The examples and results discussed above have several limitations that should be stated. Due to hardware limitations, in current systems, TDI and B-mode images cannot be acquired at exactly the same time point, even if data capture is in the simultaneous mode. In fact, ultrasound pulses for B-mode image forming and TDI are interleaved and depending on the specific approach to interleaving, the acquisition delay between B-mode and TDI images may vary. Despite this limitation, in a breath-hold acquisition, TDI images are close to the B-mode images and the acquisition difference is in the microsecond range, with both images being acquired in 15-20 ms (depending on heart rate, frame rate, etc.). Therefore, TDIOF could potentially miss transient cardiac events that are "very short-lived." As another limitation, at this time it is not possible to extend TDIOF to three dimensions because TDI is only possible in two dimensions. The out-of-plane heart motion contributes to the 2-D TDIOF magnitude and angular errors; if and when 3-D Doppler were to become commercially available, combination of 3-D Doppler with B-mode could help to further reduce the tracking errors. Another limitation is lack of availability of ground truth applicable to in vivo images which makes the validation more difficult. Tagged MRI is a good surrogate but it is not perfect. Tagged MRI slices do not exactly overlap on echocardiographic slices and there is no accurate pixel to pixel mapping from the cardiac tissue in tagged MRI to the cardiac tissue in echocardiography. In addition, the orientation of the ultrasound transducer is not exactly the same as image orientation in tagged MRI. Furthermore, echocardiography and tagged MRI have different resolutions in space and time. An additional potential issue is that MRI and echocardiography cannot be performed simultaneously. In the examples and results discussed above, since MRI was performed immediately after echocardiography, the cardiac physiologic changes are felt to be less significant. However, heart rate variability may cause alignment problems between the images. The inventors attempted to overcome these issues by careful image acquisition and matching of the slices in space and time.

7. Conclusion

In order to increase the accuracy of the speckle tracking technique and to cope with the angle dependence of TDI, a combined approach dubbed TDIOF has been described. TDIOF is formulated based on the combination of B-mode and Doppler energy terms minimized using linear algebraic methods. TDIOF was validated extensively based on simulated images and in vivo data. The performance of TDIOF was demonstrated to be better than popular motion estimation and speckle tracking techniques in echocardiography.

Throughout this document, various references are cited. All such references are incorporated herein by reference, including the references set forth in the following list:

REFERENCES

1. D. L. Kasper, E. Braunwald, A. Fauci, Harrison's Principles of Internal Medicine, 17th edition, McGraw-Hill, New York, 2008.
2. V. Fuster, R. O'Rourke, R. Walsh, P. Poole-Wilson, Hurst's the Heart, 12th edition, McGraw Hill, New York, 2007.
3. American Heart Association, Heart disease and stroke statistics—(2009), update (at-a-glance version), http://www.americanheart.org/presenter.jhtml?identifier=3037327.
4. A. Webb, Introduction to Biomedical Imaging, John Wiley and Sons Inc., Hoboken, N.J., 2003.
5. W. R. Hedrick, D. L. Hykes, D. E. Starchman, Ultrasound Physics and Instrumentation, 4th Edition, Mosby, Chicago, 2004.
6. Suhling, M., Arigovindan, A., et al.: Myocardial motion analysis from B-mode echocardiograms. IEEE Transaction on Image Processing, vol. 14, no 2, pp. 525-553 (2005).
7. Yu, W., Yan, P., Sinusas, A. J., Thiele, K., Duncan, J. S.: Towards point-wise motion tracking in echocardiographic image sequences—Comparing the reliability of different features for speckle tracking. Medical Image Analysis, vol. 10, no. 4, pp. 495-508 (2006).
8. Paragios, N.: A level set approach for shape-driven segmentation and tracking of the left ventricle. Medical Imaging, IEEE Transactions on, vol. 22, no. 6, pp. 773-776, June (2003).
9. D. Hayat, M. Kloeckner, J. Nahum, E. Ecochard-Dugelay, J. L. Dubois-Rande, D. Jean-Francois et al., Comparison of real-time three-dimensional speckle tracking to magnetic resonance imaging in patients with coronary heart disease, Am J Cardiol, 109 (2012), pp. 180-186.
10. A. Elen, H. F. Choi, D. Loeckx, H. Gao, P. Claus, P. Suetens, F. Maes, J. D'hooge, Three-Dimensional cardiac strain estimation using spatio-temporal elastic registration of ultrasound images: A feasibility study. IEEE Transaction Medical Imaging, 27(11) (2008) 1580-1591.
11. K. Y. Esther Leung, M. G. Danilouchkine, M. van Stralen, N. de Jong, A. F. W. van der Steen, J. G. Bosch, Probabilistic framework for tracking in artifact-prone 3D echocardiograms, Medical Image Analysis, 14(6) (2010) 750-758.
12. A. Myronenko, X. Song, Point Set Registration: Coherent Point Drift, IEEE Transaction on Pattern Analysis and Machine Intelligence, 32 (12) (2010) 2262-2275.
13. N. Duchateau, M. De Craene, G. Piella, E. Silva, A. Doltra, M. Sitges, B. H. Bijnens, A. F. Frangi, A spatiotemporal statistical atlas of motion for the quantification of abnormal myocardial tissue velocities, Medical Image Analysis, 15(3) (2011) 316-328.
14. N. Bachner-Hinenzon, O. Ertracht, M. Lysiansky, O. Binah and D. Adam, Layer-specific assessment of left ventricular function by utilizing wavelet de-noising: a validation study, Medical and Biological Engineering and Computing, 49(1) (2011) 3-13.
15. I. Dydenko, F. Jamal, O. Bernard, J. D'hooge, I. E. Magnin, D. Friboulet, A level set framework with a shape and motion prior for segmentation and region tracking in echocardiography, Medical Image Analysis, 10(2) (2006) 162-177.
16. P. Yan, A. Sinusas, J. S. Duncan, Boundary element method-based regularization for recovering of LV deformation, Medical Image Analysis, 11 (6) (2007) 540-554.

17. M. De Craene, G. Piella, O. Camara, N. Duchateau, E. Silva, A. Doltra, J. D'hooge, J. Brugada, M. Sitges, A. Frangi, Temporal diffeomorphic free form deformation application to motion and strain estimation from 3D echocardiography, Medical Image Analysis, 16(2) (2012) 427-450.
18. M. Ashraf, A. Myronenko, T. Nguyen, A. Inage, W. Smith, R. I. Lowe et al., Defining left ventricular apex-to-base twist mechanics computed from high-resolution 3D echocardiography: validation against sonomicrometry, JACC Cardiovasc Imaging, 3 (2010), pp. 227-234.
19. X. Papademetris, A. J. Sinusas, P. Dione, R. T. Constable, and J. S. Duncan, Estimation of 3-D left ventricular deformation from medical images using biomechnical models, IEEE Transaction on Medical Imaging, 21(7) (2002) 786-800.
20. X. Papademetris, A. J. Sinusas, D. P. Dione, J. S. Duncan, Estimation of 3D left ventricular deformation from echocardiography, Medical Image Analysis, 5(1) (2001) 17-28.
21. S. A. Kleijn, W. P. Brouwer, M. F. Aly, I. K. Russel, G. J. de Roest, A. M. Beek et al., Comparison between three-dimensional speckle-tracking echocardiography and cardiac magnetic resonance imaging for quantification of left ventricular volumes and function, Eur Heart J Cardiovasc Imaging, 13 (2012), pp. 834-839.
22. Garcia, D., del Alamo, J. C., Tanné, D., et al: Two-Dimensional Intraventricular Flow Mapping by Digital Processing Conventional Color-Doppler Echocardiography Images. Medical Imaging, IEEE Transactions on, vol. 29, no. 10, pp. 1701-1713 (2010).
23. Dalen, H., Thorstensen, A., Aase, S A., Ingul, C. B., et al.: Segmental and global longitudinal strain and strain rate based on echocardiography of 1266 individuals: the HUNT study in Norway. Eur J Echocardiogr. Vol. 11, no. 2, pp. 76-83 (2010).
24. Amundsen, B H, Crosby, J, Steen, P A, Torp, H, Slordahl, S A, Stoylen, A: Regional myocardial long-axis strain and strain rate measured by different tissue Doppler and speckle tracking echocardiography methods: a comparison with tagged magnetic resonance imaging. Eur J Echocardiogr, vol. 10, pp. 229-37 (2009).
25. V. Fuster, R. O'Rourke, R. Walsh, P. Poole-Wilson, Hurst's the Heart, 12th edition, McGraw Hill, New York, 2007.
26. O. Catherine, Textbook of Clinical Echocardiography, Third edition, W.B. Saunders, Philadelphia, 2009.
27. D. Sutton, R. G. Grainger A Textbook of Radiology, E. S. Livingstone, Edinburgh, 2002.
28. D. Fred, A. Mettler and J. Milton, M. D. Guiberteau, Essentials of nuclear medicine imaging, Fifth edition, W.B. Saunders, Philadelphia, 2005.
29. J. A. Sorenson, M. E. Phelps, Physics in nuclear medicine, Second edition, W.B. Saunders, Philadelphia, 1987.
30. Vahid Tavakoli, Jamie Kemp, Buddha Dawn, Marcus Stoddard, Amir A. Amini, "Comparison of myocardial motion estimation methods based on simulated echocardiographic B-mode and RF data", SPIE Medical Imaging, 76260N, 2010.
31. Gao, H., Choi, H. F., Claus, P., Boonen, S., et al.: A fast convolution-based methodology to simulate 2-D/3-D cardiac ultrasound images. IEEE Transactions on Ultrasonics, Ferroelectrics and Frequency Control, vol. 56, no. 2, pp. 404-409, February (2009).
32. Arts, T., Hunter, W. C., Douglas, A., Muijtjens, A. M. M., Reneman R. S.: Description of the Deformation of the Left Ventricle by a Kinematic Model. J. Biomechanics, vol. 25, no. 10, pp. 1119-1127 (1992).
33. Vahid Tavakoli, Michael Kendrick, Motaz Alshaher, Amir Amini, A Two-Chamber Multi-modal (MR/Ultrasound) Cardiac Phantom for Normal and Pathologic Hearts, International Society of Magnetic Resonance in Medicine (ISMRM), 2012.
34. Jensen, J. A.: A model for the propagation and scattering of ultrasound in tissue. J. Acoust. Soc. Am., vol. 89, number, pp. 182-191 (1991).
35. J. A. Jensen and N. B. Svendsen: Calculation of pressure fields from arbitrarily shaped, apodized, and excited ultrasound transducers, IEEE Trans. Ultrason., Ferroelec., Freq. Contr., 39, pp. 262-267, 1992.
36. Tavakoli, V.; Negandar, M. J.; Kendrick, M.; Alshaher, M.; Stoddard, M.; Amini, A. A.; "A biventricular multi-modal (MRI/ultrasound) cardiac phantom," Engineering in Medicine and Biology Society (EMBC), 2012 Annual International Conference of the IEEE, vol., no., pp. 3187-3190, Aug. 28, 2012-Sep. 1, 2012.
37. ASE Guidelines and Standards—American Society of Echocardiography, www.asecho.org/guidelines/
38. B. Lesniak-Plewinska, S. Cygan, K. Kaluzynski, J. D'hooge, J. Zmigrodzki, E. Kowali, M. Kordybac, M. Kowalski, "A Dual-Chamber, Thick-Walled Cardiac Phantom for Use in Cardiac Motion and Deformation Imaging by Ultrasound,", Ultrasound in Medicine & Biology, vol. 36, Issue 7, pp. 1145-1156, 2010.
39. A. Amini and J. Prince (Eds.), Measurement of cardiac deformations from MRI: physical and mathematical models, Kluwer Academic Publishers, Dordrecht, 2001.
40. T. Arts, F. W. Prinzen, T. Delhaas, J. Milles, A. Rossi, P. Clarysse. Mapping displacement and deformation of the heart with local sine wave modeling. IEEE Trans Med Imag 2010 May; 29(5):1114-23.
41. Goo-Yeong Cho, Jonathan Chan, Rodel Leano, Mark Strudwick, Thomas H. Marwick, Comparison of Two-Dimensional Speckle and Tissue Velocity Based Strain and Validation With Harmonic Phase Magnetic Resonance Imaging, The American Journal of Cardiology, Volume 97, Issue 11, 1 Jun. 2006, Pages 1661-1666.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for cardiac motion estimation, comprising:
   receiving, by an image processing machine, a set of echocardiographic images of a heart, the echocardiographic images including B-mode ultrasonic images and Tissue Doppler Imaging (TDI) images;
   transforming, by the image processing machine, the set of echocardiographic images of the heart into a motion field representing the motion of the heart by simultaneously combining motion components in a plurality of directions from speckle data from the B-mode ultrasonic images and information from the TDI images; and
   outputting, to an output device, the motion field representing motion of the heart.

2. The method of claim 1,
   wherein transforming the set of echocardiographic images of the heart into the motion field utilizes an optical flow energy function which combines:
   B-mode intensity constancy;
   motion smoothness; and
   Doppler/B-mode velocity similarity.

3. The method of claim 2,
wherein B-mode intensity constancy is formulated as:

$$E_{data}=|I(p+w+dw)-I(p)|^2$$

where:
- $p=(x, y, t)$ and the flow field is $w(p)=(u(p),v(p),1)$ where u and v are the motion vectors and x, y, and t are the spatial and temporal dimensions;
- $I(p)$ is the pixel intensity at location p and $I(p+w)$ is the pixel intensity from a subsequent image at location p+w, assuming that the pixel intensity is the same along the motion vector;

which is linearized using Taylor series expansion as:

$$I_t(p+w+dw)-I(p)=I_t(p)+I_x(p)du(p)+I_y(p)dv(p)$$

with $$I_x(p) = \frac{\partial I(p+w)}{\partial x}$$

$$I_y(p) = \frac{\partial I(p+w)}{\partial y}$$

$$I_t(p)=I(p+w)-I(p);$$

wherein motion smoothness is formulated as:

$$E_s=|\nabla(u+du)|^2+|\nabla(v+dv)|^2$$

with $$|\nabla(u+du)|^2 = \left(\frac{\partial(u+du)}{\partial x}\right)^2 + \left(\frac{\partial(u+du)}{\partial y}\right)^2;$$

and
wherein Doppler/B-mode velocity similarity is formulated as:

$$E_{tdi}=(\vec{v}^T\vec{v}_t-w_{tdi})^2=(u_tu+v_tv-w_{tdi})^2$$

where:
- $\vec{v}=(u, v)$ is the B-mode velocity;
- $\vec{v}_t=(u_t, v_t)$ is the transducer orientation; and
- $w_{tdi}$ is the TDI velocity;

such that the energy function to be minimized is:

$$E(u, v) = E_{data} + \alpha E_s + \beta\psi(E_{tdi}) =$$
$$\int_\Omega (|I(P+w+dw)-I(p)|^2 + \alpha(|\nabla(u+du)|^2 + |\nabla(v+dv)|^2) +$$
$$\beta\cdot\psi((u_t(u+du)+v_t(v+dv)-w_{tdi})^2))$$

where:
- α is the smoothness weight;
- β is the TDI/velocity correspondence parameter; and
- ψ(s) is a Geman-Mcclure penalizer to keep the range of $E_{tdi}$ between 0 and 1 where s is the input data, σ is the scaling parameter, and $$\psi(s) = \frac{s^2}{s^2+\sigma^2}.$$

4. The method of claim 3, wherein u, v, du, and dv are vectorized as U, V, dU, and dV, and the energy function is discretized.

5. The method of claim 4, wherein u, v, dU, and dV are initialized as 0, with dU and dV iteratively updated using linear least squares.

6. The method of claim 5, wherein transforming the set of echocardiographic images of the heart into the motion field is performed in a multi scale strategy, with a course scale used in an initial step and a fine scale is used in a subsequent step.

7. A system for cardiac motion estimation, comprising:
- an imaging device configured to acquire a set of echocardiographic images of a heart, the echocardiographic images including B-mode ultrasonic images and Tissue Doppler Imaging (TDI) images;
- a data storage device in communication with the imaging device and configured to store the set of echocardiographic images; and
- an image processing machine in communication with the data storage device and configured to calculate a motion field representing the motion of the heart by simultaneously combining motion components in a plurality of directions from speckle data from the B-mode ultrasonic images and information from the TDI images.

8. The system of claim 7, wherein the image processing machine calculates the motion field utilizing an optical flow energy function which combines:
- B-mode intensity constancy;
- motion smoothness; and
- Doppler/B-mode velocity similarity.

9. The system of claim 8,
wherein B-mode intensity constancy is formulated as:

$$E_{data}=|I(p+w+dw)-I(p)|^2$$

where:
- $p=(x, y, t)$ and the flow field is $w(p)=(u(p),v(p),1)$ where u and v are the motion vectors and x, y, and t are the spatial and temporal dimensions;
- (p) is the pixel intensity at location p and I(p+w) is the pixel intensity from a subsequent image at location p+w, assuming that the pixel intensity is the same along the motion vector;

which is linearized using Taylor series expansion as:

$$I_t(p+w+dw)-I(p)=I_t(p)+I_x(p)du(p)+I_y(p)dv(p)$$

with $$I_x(p) = \frac{\partial I(p+w)}{\partial x}$$

$$I_y(p) = \frac{\partial I(p+w)}{\partial y}$$

$$I_t(p)=I(p+w)-I(p);$$

wherein motion smoothness is formulated as:

$$E_s=|\nabla(u+du)|^2+|\nabla(v+dv)|^2$$

with $$|\nabla(u+du)|^2 = \left(\frac{\partial(u+du)}{\partial x}\right)^2 + \left(\frac{\partial(u+du)}{\partial y}\right)^2;$$

and wherein Doppler/B-mode velocity similarity is formulated as:

$$E_{tdi}=(\vec{v}^T\vec{v}_t-w_{tdi})^2=(u_tu+v_tv-w_{tdi})^2$$

where:

$\vec{v}=(u, v)$ is the B-mode velocity;
$\vec{v}_t=(u_t, v_t)$ is the transducer orientation; and
$w_{tdi}$ is the TDI velocity;

such that the energy function to be minimized is:

$$E(u,v) = E_{data} + \alpha E_s + \beta\psi(E_{tdi}) =$$
$$\int_\Omega (|I(P+w+dw)-I(p)|^2 + \alpha(|\nabla(u+du)|^2 + |\nabla(v+dv)|^2) +$$
$$\beta\cdot\psi((u_t(u+du)+v_t(v+dv)-w_{tdi})^2))$$

where:

α is the smoothness weight;
β is the TDI/velocity correspondence parameter; and
ψ(s) is a Geman-Mcclure penalizer to keep the range of $E_{tdi}$ between 0 and 1 where s is the input data, σ is the scaling parameter, and $$\psi(s) = \frac{s^2}{s^2+\sigma^2}.$$

10. The system of claim 9, wherein u, v, du, and dv are vectorized as U, V, dU, and dV, and the energy function is discretized.

11. The system of claim 10, wherein u, v, dU, and dV are initialized as 0 with dU and dV iteratively updated using linear least squares.

12. The system of claim 11, wherein calculating the motion field is performed in a multiscale strategy, with a course scale used in an initial step and a fine scale is used in a subsequent step.

13. The system of claim 7, further comprising an output device in communication with the image processing machine and configured to display the motion field representing the motion of the heart.

* * * * *

UNITED STATES PATENT AND TRADEMARK OFFICE
CERTIFICATE OF CORRECTION

Page 1 of 1

PATENT NO. : 9,629,615 B1
APPLICATION NO. : 14/480313
DATED : April 25, 2017
INVENTOR(S) : Vahid Tavakoli et al.

It is certified that error appears in the above-identified patent and that said Letters Patent is hereby corrected as shown below:

In the Claims

Claim 3, Column 30, Line 40-43, replace:

$(p)$ is the pixel intensity at location p and $I(p + w)$ is the pixel intensity from a subsequent image at location p + w, assuming that the pixel intensity is the same along the motion vector;

With:

$I(p)$ is the pixel intensity at location p and $I(p + w)$ is the pixel intensity from a subsequent image at location p + w, assuming that the pixel intensity is the same along the motion vector;

Signed and Sealed this
Twenty-seventh Day of June, 2017

Joseph Matal
*Performing the Functions and Duties of the
Under Secretary of Commerce for Intellectual Property and
Director of the United States Patent and Trademark Office*